(12) United States Patent
Hanley

(10) Patent No.: US 8,993,316 B2
(45) Date of Patent: Mar. 31, 2015

(54) METHODS AND COMPOSITIONS FOR GENE THERAPY AND GHRH THERAPY

(76) Inventor: Brian P. Hanley, Davis, CA (US)

( * ) Notice: Subject to any disclaimer, the term of this patent is extended or adjusted under 35 U.S.C. 154(b) by 108 days.

(21) Appl. No.: 13/298,257

(22) Filed: Nov. 16, 2011

(65) Prior Publication Data

US 2013/0122105 A1 May 16, 2013

(51) Int. Cl.
| | |
|---|---|
| *C12N 15/63* | (2006.01) |
| *C12N 15/85* | (2006.01) |
| *A61K 48/00* | (2006.01) |
| *A61K 45/06* | (2006.01) |
| *C07K 14/47* | (2006.01) |
| *A61K 9/16* | (2006.01) |
| *C07K 14/60* | (2006.01) |

(52) U.S. Cl.
CPC ............... *C12N 15/85* (2013.01); *C12N 15/63* (2013.01); *A61K 9/1641* (2013.01); *A61K 9/1647* (2013.01); *A61K 45/06* (2013.01); *A61K 48/0008* (2013.01); *A61K 48/0075* (2013.01); *C07K 14/60* (2013.01); *C07K 14/4716* (2013.01); *C12N 2800/24* (2013.01); *C12N 2830/008* (2013.01); *C12N 2830/85* (2013.01)
USPC ........ 435/320.1; 424/489; 424/499; 514/44 R

(58) Field of Classification Search
CPC ......... A61K 9/14; A61K 48/00; C12N 15/63; C12N 15/85
USPC ............... 435/320.1; 424/489, 499; 514/44 R
See application file for complete search history.

(56) References Cited

U.S. PATENT DOCUMENTS

| | | | |
|---|---|---|---|
| 5,298,422 A | 3/1994 | Schwartz et al. | |
| 5,756,264 A | 5/1998 | Schwartz et al. | |
| 6,423,693 B1 | 7/2002 | Schwartz et al. | |
| 6,551,996 B1 | 4/2003 | Schwartz et al. | |
| 6,759,393 B1 | 7/2004 | Morsey et al. | |
| 7,166,461 B2 | 1/2007 | Schwartz et al. | |
| 7,241,744 B2 | 7/2007 | Draghia-Akli et al. | |
| 7,245,963 B2 | 7/2007 | Draghia-Akli et al. | |
| 7,250,405 B2 | 7/2007 | Draghia-Akli et al. | |
| 7,316,925 B2 | 1/2008 | Draghia-Akli et al. | |
| 7,338,656 B2 | 3/2008 | Draghia-Akli et al. | |
| 7,351,815 B2 | 4/2008 | Fisher et al. | |
| 7,361,642 B2 | 4/2008 | Draghia-Akli et al. | |
| 7,468,273 B2 | 12/2008 | Fisher et al. | |
| 7,494,805 B2 | 2/2009 | Sisk et al. | |
| 7,517,863 B2 | 4/2009 | Draghia-Akli et al. | |
| 7,664,545 B2 | 2/2010 | Westersten et al. | |
| 7,846,720 B2 | 12/2010 | Draghia-Akli et al. | |
| 7,893,025 B2 | 2/2011 | Lussier et al. | |
| 2006/0188988 A1* | 8/2006 | Draghia-Akli et al. ....... 435/455 |
| 2009/0170748 A1 | 7/2009 | Draghia-Akli et al. | |
| 2010/0010467 A1 | 1/2010 | Draghia-Akli et al. | |
| 2011/0034544 A1 | 2/2011 | Draghia-Akli et al. | |

OTHER PUBLICATIONS

S Fukunaga, G Kanda, J Tanase, H Harashima, T Ohyama and H Kamiya, "A designed curved DNA sequence remarkably enhances transgene expression from plasmid DNA in mouse liver", Gene Therapy, Sep. 15, 2011, http://dx.doi.org/10.1038/gt.2011.127 Published by: Macmillan Publishers Limited, USA.
J. Nishikawa, M. Amano, Y. Fukue, S. Tanaka, H. Kishi, Y. Hirota, K. Yoda & T. Ohyama, "Left-handedly curved DNA regulates accessibility to cis-DNA elements in chromatin", Nucleic Acids Research, Nov. 15, 2003, Vo. 31, No. 22, pp. 6651-6662, Published by: Oxford University Press, UK.
Z. Zou, P.D. Sun, "An improved recombinant mammalian cell expression system for human transforming growth factor-2 and -3 preparations.", Protein Expression & Purification, Apr. 25, 2006, doi:10.1016/j.pep.2006.06.022., Online, published by: Elsevier Inc.
N. Sumida, J. Nishikawa, H. Kishi, M. Amano, T. Furuya, H. Sonobe & T. Ohyama, "A designed curved DNA segment that is a remarkable activator of eukaryotic transcription", The FEBS Journal, Dec. 2006, vol. 273, Issue 24, pp. 5691-5702, doi: 10.1111/j.1742-4658.2006. 05557.x, Published by: Wiley, USA.
B.Yu, J. Becnel, M. Zerfaoui, R. Rohatgi, A. H. Boulares, C.D. Nichols, "Serotonin 5-Hydroxytryptamine2A Receptor Activation Suppresses Tumor Necrosis Factor-α-Induced Inflammation with Extraordinary Potency", J. of Pharmacology and Experimental Therapeutics, Nov. 2008, doi: 10.1124/jpet.108.143461, vol. 327, No. 2, pp. 316-323, Published by: Am. Soc. for Pharm. & Exp. Therapeutics.
C.L. Brazolot-Millan, R. Weeratna, A.M. Krieg, C.-A. Siegrist, & H. L. Davis, "CpG DNA can induce strong Th1 humoral and cell-mediated immune responses against hepatitis B surface antigen in young mice", PNAS, Dec. 1998, vol. 95, Issue 26, pp. 15553-15558, doi: 10.1073/pnas.95.26.15553, Published by: National Academy of Sciences.
P. De Felipe, "Skipping the co-expression problem: the new 2A 'CHYSEL' technology", Genetic Vaccines and Therapy, Sep. 13, 2004, vol. 2, Paper 13, doi:10.1186/1479-0556-2-13, Published by: Biomed Central, U.K.
M.A. Tracy, K.L. Ward, L. Firouzabadian, Y. Wang, N. Dong, R. Qian, Y. Zhang, "Factors affecting the degradation rate of poly(lactide-co-glycolide) microspheres in vivo and in vitro", Biomaterials. Jun. 1999, vol. 20, Issue 11, pp. 1057-1062, doi:10. 1016/50142-9612(99)00002-2, Published by: Elsevier, Netherlands.
A. Vila, A. Sanchez, C. Perez & M. J. Alonso, "PLA-PEG Nanospheres: New Carriers for Transmucosal Delivery of Proteins and Plasmid DNA", Polymers for Advanced Technologies, Jan. 2002, vol. 13, Issue 1112, pp. 851-858, doi:10.1002/pat.280, Wiley Interscience, USA.

* cited by examiner

*Primary Examiner* — Janet Epps-Smith
(74) *Attorney, Agent, or Firm* — Matthew J. Temmerman; Temmerman Law Office

(57) ABSTRACT

A composition and method comprising an anti-adjuvant such as DOI (an anti-inflammatory) together with any gene therapy plasmid is disclosed. A method for GHRH production in-vivo using a set of compositions and methods for use of those compositions is provided.

6 Claims, 2 Drawing Sheets

SEQUENCE LISTING

<160> NUMBER OF SEQ ID NOS: 30

<210> SEQ ID NO 1
<211> LENGTH: 462
<212> TYPE: DNA
<213> ORGANISM: Homo sapiens
<220> FEATURE:
<221> NAME/KEY: gene
<223> OTHER INFORMATION: Homo sapiens growth hormone releasing hormone
      (GHRH), transcript variant 1, mRNa (NCBI Reference Sequence:
      NM_021081.)

<400> SEQUENCE: 1

| | | |
|---|---|---|
| gtgaaggatg ccactctggg tgttcttctt tgtgatcctc accctcagca | 50 |
| acagctccca ctgctcccca cctccccctt tgaccctcag gatgcggcgg | 100 |
| tatgcagatg ccatcttcac caacagctac cggaaggtgc tgggccagct | 150 |
| gtccgcccgc aagctgctcc aggacatcat gagcaggcag cagggagaga | 200 |
| gcaaccaaga gcgaggagca agggcacggc ttggtcgtca ggtagacagc | 250 |
| atgtgggcag aacaaaagca aatggaattg gagagcatcc tggtggccct | 300 |
| gctgcagaag cacagcagga actcccaggg atgaagattc ctcctgtgac | 350 |
| ccgggctacc tgtagccaaa atgcaactgg atccagttaa tcctctcatt | 400 |
| tctgacccac ttttttcctttt gaaaatacaa taaaattccc ccataccggt | 450 |
| gtgcatttaa aa | 462 |

<210> SEQ ID NO 2
<211> LENGTH: 452
<212> TYPE: DNA
<213> ORGANISM: Homo sapiens
<220> FEATURE:
<221> NAME/KEY: gene
<223> OTHER INFORMATION: Homo sapiens growth hormone releasing hormone
      (GHRH), transcript variant 2, mRNa (NCBI Reference Sequence:
      NM_001184731))

<400> SEQUENCE: 2

| | | |
|---|---|---|
| atgccactct gggtgttctt ctttgtgatc ctcaccctca gcaacagctc | 50 |
| ccactgctcc ccacctcccc ctttgaccct caggatgcgg cggtatgcag | 100 |
| atgccatctt caccaacagc taccggaagg tgctgggcca gctgtccgcc | 150 |
| cgcaagctgc tccaggacat catgagcagg cagcagggag agagcaacca | 200 |
| agagcgagga gcaagggcac ggcttggtcg tcaggtagac agcatgtggg | 250 |
| cagaacaaaa gcaaatggaa ttggagagca tcctggtggc cctgctgcag | 300 |
| aagcacagga actcccaggg atgaagattc ctcctgtgac ccgggctacc | 350 |
| tgtagccaaa atgcaactgg atccagttaa tcctctcatt tctgacccac | 400 |
| ttttttcctttt gaaaatacaa taaaattccc ccataccggt gtgcatttaa | 450 |
| aa | 452 |

<210> SEQ ID NO 3
<211> LENGTH: 456
<212> TYPE: DNA
<213> ORGANISM: artificial sequence
<220> FEATURE:
<221> NAME/KEY: cDS
<223> OTHER INFORMATION: Homo sapiens derived human GHRH optimized for
      minimal immune system stimulation

<400> SEQUENCE: 3

```
atgccactct gggtgttctt ctttgtgatc ctcaccctca gcaacagctc          50
ccactgctcc ccacctcccc ctttgaccct caggatgagg agatatgcag         100
atgccatctt caccaacagc tacaggaagg ttctgggcca gctgtctgcc         150
aggaagctgc tccaggacat catgagcagg cagcagggag agagcaacca         200
agagagagga gcaagggcaa gacttggtag gcaagtagac agcatgtggg         250
cagaacaaaa gcaaatggaa ttggagagca tcctggtggc cctgctgcag         300
aagcacagca ggaactccca gggatgaaga ttcctcctgt gaccagggaa         350
ttcctgtagc caaaatgcaa ctggatccag ttaatcctct catttctgac         400
ccactttttc ctttgaaaat acaataaaat tcccccatac aggtgtgcat         450
ttaaaa                                                         456

<210> SEQ ID NO 4
<211> LENGTH: 452
<212> TYPE: DNA
<213> ORGANISM: artificial sequence
<220> FEATURE:
<221> NAME/KEY: cDS
<223> OTHER INFORMATION: Homo sapiens derived human GHRH optimized for
      minimal immune system stimulation

<400> SEQUENCE: 4
atgccactct gggtgttctt ctttgtgatc ctcaccctca gcaacagctc          50
ccactgctcc ccacctcccc ctttgaccct caggatgagg agatatgcag         100
atgccatctt caccaacagc tacaggaagg tgctgggcca gctgtctgcc         150
agaaagctgc tccaggacat catgagcagg cagcagggag agagcaacca         200
agagagagga gcaagggcaa ggcttggtag acaggtagac agcatgtggg         250
cagaacaaaa gcaaatggaa ttggagagca tcctggtggc cctgctgcag         300
aagcacagga actcccaggg atgaagattc ctcctgtgac cagggctacc         350
tgtagccaaa atgcaactgg atccagttaa tcctctcatt tctgacccac         400
tttttccttt gaaaatacaa taaaattccc ccatacaaat gtgcatttaa         450
aa                                                             452

<210> SEQ ID NO 5
<211> LENGTH: 228
<212> TYPE: DNA
<213> ORGANISM: artificial sequence
<220> FEATURE:
<221> NAME/KEY: cDS
<223> OTHER INFORMATION: Homo sapiens derived human GHRH optimized for
      minimal immune system stimulation

<400> SEQUENCE: 5
atgcctctgt gggtgttctt ctttgtgatc ctgaccctga gcaacagcag          50
ccactgcagc ccacctccac ctctgaccct gaggatgagg aggtatgcag         100
atgccatctt caccaacagc tacagaaagg tgctgggcca gctgagtgcc         150
agaaagctgc tgcaggacat catgagcagg cagcagggtg agagcaacca         200
ggagagggga gccagagcca ggctgtga                                 228

<210> SEQ ID NO 6
<211> LENGTH: 410
<212> TYPE: DNA
```

<213> ORGANISM: Homo Sapiens
<220> FEATURE:
<221> NAME/KEY: promoter
<223> OTHER INFORMATION: Human actin alpha 1 (acta1) Promoter fragment
      from chromosome 1 (NCBI Ref Seq Ng_006672)

<400> SEQUENCE: 6

| gcaccttccc gagcgcccag ggcgctcaga gtggacatgg ttggggaggc | 50 |
| ctttgggaca ggtgcggttc ccggagcgca ggcgcacaca tgcacccacc | 100 |
| ggcgaacgcg gtgaccctcg ccccacccca tcccctccgg cgggcaactg | 150 |
| ggtcgggtca ggaggggcaa acccgctagg gagacactcc atatacggcc | 200 |
| cggcccgcgt tacctgggac cgggccaacc cgctccttct ttggtcaacg | 250 |
| caggggaccc gggcggggc ccaggccgcg aaccggccga gggaggggc | 300 |
| tctagtgccc aacacccaaa tatggctcga aagggcagc gacattcctg | 350 |
| cggggtggcg cggagggaat gcccgcgggc tatataaaac ctgagcagag | 400 |
| ggacaagcgg | 410 |

<210> SEQ ID NO 7
<211> LENGTH: 416
<212> TYPE: DNA
<213> ORGANISM: artificial sequence
<220> FEATURE:
<221> NAME/KEY: promoter
<223> OTHER INFORMATION: Human (acta1) Promoter optimized for minimal
      immune system stimulation

<400> SEQUENCE: 7

| gggaccttcc ccagccccca gggccctcag agtggacatg gttggggagg | 50 |
| cctttgggac aggtgcagtt cccagagtct cagacacaca catccaccca | 100 |
| ccagtgaaca ctgtgaccct caccccaccc catcccctcc agtgggcaac | 150 |
| tgggttgggt caggagggga aaaccccta gggagacact ccatatactg | 200 |
| cccagaccaa gttacctggg accaggccaa ccctctcctt ctttggtcaa | 250 |
| cccaggggac cctggcaggg gcccaggact caaaccagtc aagggagggg | 300 |
| ggtctagtgc ccaacaccca aatatggctc aagaagggca gcaacattcc | 350 |
| tgctgggtgg cccagaggga atgcccccag gttatataaa acctgaccag | 400 |
| agggacaagc tgccag | 416 |

<210> SEQ ID NO 8
<211> LENGTH: 70
<212> TYPE: DNA
<213> ORGANISM: mus musculus
<220> FEATURE:
<221> NAME/KEY: sig_peptide
<223> OTHER INFORMATION: Ig kappa secretion signal fragment

<400> SEQUENCE: 8

| ctcagagatg gagacagaca cactcctgct atgggtgctg ctgctctggg | 50 |
| ttccaggttc cactggtgac | 70 |

<210> SEQ ID NO 9
<211> LENGTH: 40
<212> TYPE: DNA
<213> ORGANISM: artificial sequence
<220> FEATURE:
<221> NAME/KEY: promoter
<223> OTHER INFORMATION: at rich variant of t promoter preamble optmized for minimum immune system stimulation

<400> SEQUENCE: 9 tcagttttc atgtttttca tgtttttcat gtttttcaca         40

<210> SEQ ID NO 10
<211> LENGTH: 836
<212> TYPE: DNA
<213> ORGANISM: artificial sequence
<220> FEATURE:
<221> NAME/KEY: promoter
<223> OTHER INFORMATION: at rich variant of t promoter preamble optmized
      for minimum immune system stimulation repeated 21x

<400> SEQUENCE: 10 tcagttttc atgtttttca tgtttttcat gtttttcaca tcagttttc         50
atgtttttca tgtttttcat gtttttcaca tcagttttc atgtttttca         100
tgtttttcat gtttttcaca tcagttttc atgtttttca tgtttttcat         150
gtttttcaca tcagttttc atgtttttca tgtttttcat gtttttcaca         200
tcagttttc atgtttttca tgtttttcat gtttttcaca tcagttttc         250
atgtttttca tgtttttcat gtttttcaca tcagttttc atgtttttca         300
tgtttttcat gtttttcaca tcagttttc atgtttttca tgtttttcat         350
gtttttcaca tcagttttc atgtttttca tgtttttcat gtttttcaca         400
tcagttttc atgtttttca tgtttttcat gtttttcaca tcagttttc         450
atgtttttca tgtttttcat gtttttcaca tcagttttc atgtttttca         500
tgtttttcat gtttttcaca tcagttttc atgtttttca tgtttttcat         550
gtttttcaca tcagttttc atgtttttca tgtttttcat gtttttcaca         600
tcagttttc atgtttttca tgtttttcat gtttttcaca tcagttttc         650
atgtttttca tgtttttcat gtttttcaca tcagttttc atgtttttca         700
tgtttttcat gtttttcaca tcagttttc atgtttttca tgtttttcat         750
gtttttcaca tcagttttc atgtttttca tgtttttcat gtttttcaca         800
tcagttttc atgtttttca tgtttttcat gttttt         836

<210> SEQ ID NO 11
<211> LENGTH: 400
<212> TYPE: DNA
<213> ORGANISM: artificial sequence
<220> FEATURE:
<221> NAME/KEY: misc_feature
<223> OTHER INFORMATION: at rich sequence 1 - synthetic

<400> SEQUENCE: 11
acctaggtct agcttttttt aattttcaaa atcatacaa ttacccattc         50
atacaatcct ctccatttca actaaactac ttcaccttct actagactta         100
ctcttgtctt cctaatccaa tatacctaaa tattcacttt ctataataac         150
cctctataaa ataatcttaa cctctcccaa aacttaataa caattttctc         200
caaatctctc actcctacca ctttcacatc tacattccac cacacttccc         250
ctcataatta aacctaacta actttaccac tatcaacata cattcacccc         300
ccaccctcaa ccacctacca tactcattta acatactact caccacttcc         350
ctaaacacat atcactcatc aatttatttt tttcaccaag aggatctttc         400

<210> SEQ ID NO 12
<211> LENGTH: 400
<212> TYPE: DNA
<213> ORGANISM: artificial sequence
<220> FEATURE:
<221> NAME/KEY: misc_feature
<223> OTHER INFORMATION: at rich sequence 2

<400> SEQUENCE: 12

| | | |
|---|---|---|
| tccaattttt taataacacc acccctcatc taccccaaac tactgagaat | 50 |
| ctaattatat ctacattcac ttacatatcc atctccaccc tccctcaata | 100 |
| gtctctacac cagatgttgt cttatattgt ttaccttcca tacactttca | 150 |
| tatcttacaa cctttccatc ctatccaaac aaattatcac accatctaac | 200 |
| taacactgat agaaccaata cttatcactt ctcactcata caaaccaatt | 250 |
| ccaacaaaaa accaccatca cacctaccaa tccctaacat acccccctca | 300 |
| atctaatata ttctttaata taactttaaa tatcccaaat actccttcct | 350 |
| tatacccctaa acagtgttaa tagtcatctg tcccacctt ttttcccata | 400 |

<210> SEQ ID NO 13
<211> LENGTH: 1168
<212> TYPE: DNA
<213> ORGANISM: artificial sequence
<220> FEATURE:
<221> NAME/KEY: cDS
<223> OTHER INFORMATION: Modified for minimum immune system stimulation
      Derived from E. coli Kanamycin resistance gene

<400> SEQUENCE: 13

| | | |
|---|---|---|
| tagtcaccct ccaacaccag ctgactctcc ctgactggct tgtctgctcc | 50 |
| aggcatcagc ttacagacaa gctgtgaagt ctcctggagc tgcatgtgtc | 100 |
| agaggtttc acagtcatca cagaaactgg ctagactaaa gggcctagtg | 150 |
| atactcctat ttttataggt taatgtcatg ataataatgg tttcttagaa | 200 |
| gtcaggtggc acttttctgg gaaatgtgct ctgaacccct atttgtttat | 250 |
| ttttctaaat acattcaaat atgtatcagc tcatgagaca ataaccctga | 300 |
| taaatgcttc aataatcctc agtaatacaa ggggtgttag gtaccaatga | 350 |
| gccatattca aagggaaact tcttgctcta ggccaagatt aaattccaac | 400 |
| atggatgctg atttatatgg gtataaatgg gctagagata atgttgggca | 450 |
| atcaggtgca acaatctata gattgtatgg gaagccagat gctccagagt | 500 |
| tgtttctgaa acatggcaaa ggtagtgttg ccaatgatgt tacagatgag | 550 |
| atggtcagac taaactggct gacagaattt atgcctcttc ctaccatcaa | 600 |
| gcatttatc aggactcctg atgatgcatg gttactcacc actgctatcc | 650 |
| ctgggaaaac agcattccag gtattagaag aatatcctga ttcaggtgaa | 700 |
| aatattgttg atgctctggc agtgttcctg aggagattgc attctattcc | 750 |
| tgtttgtaat tgtccttta acagtgatag agtatttaga ctggctcagg | 800 |
| cacaatcaag aatgaataat ggtttggttg atgctagtga ttttgatgat | 850 |
| gagaggaatg gctggcctgt tgaacaagtc tggaaagaaa tgcataagct | 900 |
| tttgccattc tcacaggatt cagttgtcac tcatggtgat ttctcacttg | 950 |
| ataaccttat ttttgatgag gggaaattaa taggttgtat tgatgttgga | 1000 |

| | |
|---|---:|
| agagttggaa tagcagacag ataccaggat cttgccatcc tatggaactg | 1050 |
| ccttggtgag ttttctcctt cattacagaa gaggcttttt caaaaatatg | 1100 |
| gtattgataa tcctgatatg aataaattgc agtttcattt gatgctggat | 1150 |
| gagttttcct aatcagaa | 1168 |

<210> SEQ ID NO 14
<211> LENGTH: 918
<212> TYPE: DNA
<213> ORGANISM: artificial sequence
<220> FEATURE:
<221> NAME/KEY: CDS
<223> OTHER INFORMATION: Modified for minimum immune system stimulation
      short version Derived from E. coli Kanamycin resistance gene

<400> SEQUENCE: 14

| | |
|---|---:|
| atgagccata ttcaaaggga aacttcttgc tctaggccaa gattaaattc | 50 |
| caacatggat gctgatttat atgggtataa atgggctaga gataatgttg | 100 |
| ggcaatcagg tgcaacaatc tatagattgt atgggaagcc agatgctcca | 150 |
| gagttgtttc tgaaacatgg caaggtagt gttgccaatg atgttacaga | 200 |
| tgagatggtc agactaaaact ggctgacaga atttatgcct cttcctacca | 250 |
| tcaagcattt tatcaggact cctgatgatg catggttact caccactgct | 300 |
| atccctggga aaacagcatt ccaggtatta gaagaatatc ctgattcagg | 350 |
| tgaaaatatt gttgatgctc tggcagtgtt cctgaggaga ttgcattcta | 400 |
| ttcctgtttg taattgtcct tttaacagtg atagagtatt tagactggct | 450 |
| caggcacaat caagaatgaa taatggtttg ttgatgctga gtgatttga | 500 |
| tgatgagagg aatggctggc ctgttgaaca agtctggaaa gaaatgcata | 550 |
| agcttttgcc attctcacag gattcagttg tcactcatgg tgatttctca | 600 |
| cttgataacc ttatttttga tgaggggaaa ttaataggtt gtattgatgt | 650 |
| tggaagagtt ggaatagcag acagatacca ggatcttgcc atcctatgga | 700 |
| actgccttgg tgagttttct ccttcattac agaagaggct ttttcaaaaa | 750 |
| tatggtattg ataatcctga tatgaataaa ttgcagtttc atttgatgct | 800 |
| ggatgagttt ttctaatcag aattggttaa ttggttgtaa cactggcaac | 850 |
| cagtgagtgt gggtcttgca gtatcattgc agcactgggg ccagatggta | 900 |
| agcccctcctg tatcatag | 918 |

<210> SEQ ID NO 15
<211> LENGTH: 534
<212> TYPE: DNA
<213> ORGANISM: artificial sequence
<220> FEATURE:
<221> NAME/KEY: CDS
<223> OTHER INFORMATION: Modified for minimum immune system stimulation
      Derived from E. coli gentamycin resistance gene

<400> SEQUENCE: 15

| | |
|---|---:|
| atgctgagat cttctaatga gtgtgactca g cagggttcta gaccaaaaac | 50 |
| taaactgggt ggttcttcta tgggtattat tagaacttgt agactgggtc | 100 |
| cagatcaggt gaaatctatg agagcagcac tggatctgtt tggtagagaa | 150 |
| tttggtgatg tggcaactta ttctcagcat cagccagatt ctgattatct | 200 |
| gggtaatctg ctgagatcta aaacttttat tgcactggca gcatttgatc | 250 |

| | |
|---|---|
| aggaagcagt ggtgggtgca ctggcagcat atgtgctgcc aagatttgaa | 300 |
| cagccaagat ctgaaattta tatttatgat ctggcagtgt ctggtgaaca | 350 |
| tagaagacag ggtattgcaa ctgcactgat taatctgctg aaacatgaag | 400 |
| caaatgcact gggtgcatat gtgatttatg tgcaggcaga ttatggtgat | 450 |
| gatccagcag tggcactgta tactaaactg ggtattagag aagaagtgat | 500 |
| gcattttgat attgatccat ctactgcaac ttga | 534 |

<210> SEQ ID NO 16
<211> LENGTH: 534
<212> TYPE: DNA
<213> ORGANISM: artificial sequence
<220> FEATURE:
<221> NAME/KEY: cDS
<223> OTHER INFORMATION: Optimized for minimal immune system stimulation Derived from E. coli gentamycin, kanamyicin & tobramycin resistance

<400> SEQUENCE: 16

| | |
|---|---|
| atggatacta ctcaggtgac tctgattcat aaaattctgg cagcagcaga | 50 |
| tgaaagaaac ctgccactgt ggattggtgg tggttgggca attgatgcaa | 100 |
| gactgggtag agtgactaga aaacatgatg atattgatct gacttttcca | 150 |
| ggtgaaagaa gaggtgaact ggaagcaatt gtggaaatgc tgggtggtag | 200 |
| agtgatggaa gaactggatt atggttttct ggcagaaatt ggtgatgaac | 250 |
| tgctggattg tgaaccagca tggtgggcag atgaagcata tgaaattgca | 300 |
| gaagcaccac agggtagctg cccagaagca gcagaaggtg tgattgcagg | 350 |
| tagaccagtg agatgcaaca gctgggaagc aattatttgg gattattttt | 400 |
| attatgcaga tgaagtgcca ccagtggatt ggccaactaa acatattgaa | 450 |
| agctatagac tggcatgcac tagcctgggt gcagaaaaag tggaagtgct | 500 |
| gagagcagca tttagaagca gatatgcagc atga | 534 |

<210> SEQ ID NO 17
<211> LENGTH: 861
<212> TYPE: DNA
<213> ORGANISM: artificial sequence
<220> FEATURE:
<221> NAME/KEY: cDS
<223> OTHER INFORMATION: Optimized for minimal immune system stimulation Derived from E. coli ampicillin resistance gene

<400> SEQUENCE: 17

| | |
|---|---|
| atgtctattc agcattttag agtggcactg attccatttt ttgcagcatt | 50 |
| ttgcctgcca gtgtttgcac atccagaaac tctggtgaaa gtgaaagatg | 100 |
| cagaagatca gctgggtgca agagtgggtt atattgaact ggatctgaac | 150 |
| tctggtaaaa ttctggaatc ttttagacca gaagaaagat ttccaatgat | 200 |
| gtctactttt aaagtgctgc tgtgtggtgc agtgctgtct agaattgatg | 250 |
| caggtcagga acagctgggt agaagaattc attattctca gaatgatctg | 300 |
| gtggaatatt ctccagtgac tgaaaaacat ctgactgatg gtatgactgt | 350 |
| gagagaactg tgctctgcag caattactat gtctgataac actgcagcaa | 400 |
| acctgctgct gactactatt ggtggtccaa agaactgac tgcatttctg | 450 |
| cataacatgg gtgatcatgt gactagactg gatagatggg aaccagaact | 500 |

```
gaatgaagca attccaaatg atgaaagaga tactactatg ccagtggcaa        550
tggcaactac tctgagaaaa ctgctgactg gtgaactgct gactctggca        600
tctagacagc agctgattga ttggatggaa gcagataaag tggcaggtcc        650
actgctgaga tctgcactgc cagcaggttg gtttattgca gataaatctg        700
gtgcaggtga agaggttct agaggtatta ttgcagcact gggtccagat         750
ggtaaaccat ctagaattgt ggtgatttat actactggtt ctcaggcaac        800
tatggatgaa agaaacagac agattgcaga aattggtgca tctctgatta        850
aacattggtg a                                                  861

<210> SEQ ID NO 18
<211> LENGTH: 798
<212> TYPE: DNA
<213> ORGANISM: artificial sequence
<220> FEATURE:
<221> NAME/KEY: CDS
<223> OTHER INFORMATION: Optimized for minimal immune system stimulation
      Derived from E. coli Neomycin resistance gene

<400> SEQUENCE: 18
atgggtattg aacaggatgg tctgcatgca ggttctccag cagcatgggt         50
ggaaagactg tttggttatg attgggcaca gcagactatt ggttgctctg        100
atgcagcagt gtttagactg tctgcacagg gtagaccagt gctgtttgtg        150
aaaactgatc tgtctggtgc actgaatgaa ctgcaggatg aagcagcaag        200
actgtcttgg ctggcaacta ctggtgtgcc atgtgcagca gtgctggatg        250
tggtgactga agcaggtaga gattggctgc tgctgggtga agtgccaggt        300
caggatctgc tgtcttctca tctggcacca gcagaaaaag tgtctattat        350
ggcagatgca atgagaagac tgcatactct ggatccagca acttgcccat        400 tgatcatca ggcaaaacat agaattgaaa gagcaagaac tagaatggaa         450
gcaggtctgg tggatcagga tgatctggat gaagaacatc agggtctggc        500
accagcagaa ctgtttgcaa gactgaaagc aagaatgcca gatggtgaag        550
atctggtggt gactcatggt gatgcatgcc tgccaaacat tatggtggaa        600
aatggtagat ttctggtttt tattgattgt ggtagactgg gtgtggcaga        650
tagatatcag gatattgcac tggcaactag agatattgca gaagaactgg        700
gtggtgaatg gcagatagat ttctggtgc tgtatggtat tgcagcacca        750
gattctcaga gaattgcatt ttatagactg ctggatgaat ttttttga         798

<210> SEQ ID NO 19
<211> LENGTH: 392
<212> TYPE: DNA
<213> ORGANISM: artificial sequence
<220> FEATURE:
<221> NAME/KEY: rep_origin
<223> OTHER INFORMATION: Optimized for minimal immune system stimulation
      Derived from E. coli R6K origin of replication

<400> SEQUENCE: 19
ccatgtcagc cattaagtgt tcctgtgtca ctcaaaattg ctttgagagg         50
ctctaagggc ttctcagtac attacatccc tggcttgttg tccacaacca        100
ttaaacctta aagctttaa aagccttata tattcttttt tttcttataa         150
```

| | |
|---|---:|
| aacttaaaac cttagaggct atttaagttg ctgatttata ttaattttat | 200 |
| tgttcaaaca tgagagctta gtacatgaaa catgagagct tagtacatta | 250 |
| gccatgagag cttagtacat tagccatgag ggtttagttc attaaacatg | 300 |
| agagcttagt acattaaaca tgagagctta gtacatgaaa catgagagct | 350 |
| tagtacatac tatcaacagg ttgaactgct gatcttcaga tc | 392 |

<210> SEQ ID NO 20
<211> LENGTH: 259
<212> TYPE: DNA
<213> ORGANISM: artificial sequence
<220> FEATURE:
<221> NAME/KEY: rep_origin
<223> OTHER INFORMATION: Optimized for minimal immune system stimulation
      Derived from E. coli R6K origin of replication

<400> SEQUENCE: 20

| | |
|---|---:|
| aaaccttaaa acctttaaaa gccttatata ttcttttttt tcttataaaa | 50 |
| cttaaaacct tagaggctat ttaagttgct gatttatatt aattttattg | 100 |
| ttcaaacatg agagcttagt acatgaaaca tgagagctta gtacattagc | 150 |
| catgagagct tagtacatta gccatgaggg tttagttcat taaacatgag | 200 |
| agcttagtac attaaacatg agagcttagt acatactatc aacaggttga | 250 |
| actgctgat | 259 |

<210> SEQ ID NO 21
<211> LENGTH: 389
<212> TYPE: DNA
<213> ORGANISM: artificial sequence
<220> FEATURE:
<221> NAME/KEY: rep_origin
<223> OTHER INFORMATION: Optimized for minimal immune system stimulation
      Derived from E. coli R6K origin of replication

<400> SEQUENCE: 21

| | |
|---|---:|
| catgtcagca gttaagtgtt cctgtgtcac tcaaaattgc tttgagaggc | 50 |
| tctaagggct tctcagtgag ttacatccct ggcttgttgt ccacaacagt | 100 |
| taaaccttaa aagctttaaa agccttatat attcttttttt ttcttataaa | 150 |
| acttaaaacc ttagaggcta tttaagttgc tgatttatat taattttatt | 200 |
| gttcaaacat gagagcttag taagtgaaac atgagagctt agtaagttag | 250 |
| ccatgagagc ttagtaagtt agccatgagg gtttagttag ttaaacatga | 300 |
| gagcttagta agttaaacat gagagcttag taagtgaaac atgagagctt | 350 |
| agtaagtact atcaacaggt tgaactgctg atcttcagc | 389 |

<210> SEQ ID NO 22
<211> LENGTH: 535
<212> TYPE: DNA
<213> ORGANISM: artificial sequence
<220> FEATURE:
<221> NAME/KEY: rep_origin
<223> OTHER INFORMATION: Optimized for minimal immune system stimulation
      Derived from E. coli pBR322 origin of replication

<400> SEQUENCE: 22

| | |
|---|---:|
| atcttcttga gatccttttt ttctgagagt aatctgctgc ttgcaaacaa | 50 |
| aaaaaccaca gctaccagag gtggtttgtt tgcaggatca agagctacca | 100 |
| actctttttc agaaggtaac tggcttcagc agagagcaga taccaaatac | 150 |

-continued

| | |
|---|---|
| tgtccttcta gtgtagcagt agttaggcca ccacttcaag aactctgtag | 200 |
| cacagcctac ataccctagct ctgctaatcc tgttaccagt ggctgctgcc | 250 |
| agtggagata agtagtgtct tacagggttg gactcaagaa gatagttaca | 300 |
| ggataaggag cagaggtagg gctgaaaggg gggttagtgc acacagccca | 350 |
| gcttggagag aaagacctac acagaactga gataccctaca gagtgagcta | 400 |
| tgagaaagag ccaagcttcc agaagggaga aggaggaca ggtatcaggt | 450 |
| aagaggcagg gtaggaacag gagagagcaa gagggagctt ccaggggaa | 500 |
| aagcctggta tctttatagt cctgtagggt ttagc | 535 |

<210> SEQ ID NO 23
<211> LENGTH: 3249
<212> TYPE: DNA
<213> ORGANISM: artificial sequence
<220> FEATURE:
<223> OTHER INFORMATION: plasmid p80715-5.1

<400> SEQUENCE: 23

| | |
|---|---|
| gcatgccacc taggtctagc ttttttaat tttcaaaaat catacaatta | 50 |
| cccattcata caatcctctc catttcaact aaactacttc accttctact | 100 |
| agacttactc ttgtcttcct aatccaatat acctaaatat tcactttcta | 150 |
| taataaccct ctataaaata atcttaacct ctcccaaaac ttaataacaa | 200 |
| ttttctccaa atctctcact cctaccactt tcacatctac attccaccac | 250 |
| acttcccctc ataattaaac ctaactaact ttaccactat caacatacat | 300 |
| tcacccccca ccctcaacca cctaccatac tcatttaaca tactactcac | 350 |
| cacttcccta aacacatatc actcatcaat ttatttttt caccaagagg | 400 |
| atctttctta attaagggac cttccccagc ccccagggcc ctcagagtgg | 450 |
| acatggttgg ggaggccttt gggacaggtg cagttcccag agtctcagac | 500 |
| acacacatcc acccaccagt gaacactgtg accctcaccc caccccatcc | 550 |
| cctccagtgg gcaactgggt tgggtcagga ggggaaaacc ccctagggag | 600 |
| acactccata tactgcccag accaagttac ctgggaccag gccaaccctc | 650 |
| tccttctttg gtcaacccag gggaccctgg caggggccca ggactcaaac | 700 |
| cagtcaaggg agggggggtct agtgcccaac acccaaatat ggctcaagaa | 750 |
| gggcagcaac attcctgctg ggtggcccag agggaatgcc cccaggttat | 800 |
| ataaaacctg accagaggga caagctgcca ccaaaggtgg gatccccatg | 850 |
| ccactctggg tgttcttctt tgtgatcctc accctcagca acagctccca | 900 |
| ctgctcccca cctcccccctt tgaccctcag gatgaggaga tatgcagatg | 950 |
| ccatcttcac caacagctac aggaaggttc tgggccagct gtctgccagg | 1000 |
| aagctgctcc aggacatcat gagcaggcag cagggagaga gcaaccaaga | 1050 |
| gagaggagca agggcaagac ttggtaggca agtagacagc atgtgggcag | 1100 |
| aacaaaagca aatggaattg gagagcatcc tggtggccct gctgcagaag | 1150 |
| cacagcagga actcccaggg atgaagattc ctcctgtgac cagggaattc | 1200 |
| ctgtagccaa aatgcaactg gatccagtta atcctctcat ttctgaccca | 1250 |
| cttttttcctt tgaaaataca ataaaattcc cccatacagg tgtgcattta | 1300 |

```
aagcccatgg ctccaattttt ttaataacac caccccctcat ctaccccaaa      1350
ctactgagaa tctaattata tctacattca cttacatatc catctccacc      1400
ctccctcaat agtctctaca ccagatgttg tcttatattg tttacctttc      1450
atacactttc atatcttaca acctttccat cctatccaaa caaattatca      1500
caccatctaa ctaacactga tagaaccaat acttatcact tctcactcat      1550
acaaaccaat tccaacaaaa aaccaccatc acacctacca atccctaaca      1600
taccccctc aatctaatat attctttaat ataactttaa atatcccaaa       1650
tactccttcc ttatacccta aacagtgtta atagtcatct gtcccacctt      1700
tttttcccat actagtcacc ctccaacacc agctgactct ccctgactgg      1750
cttgtctgct ccaggcatca gcttacagac aagctgtgaa gtctcctgga      1800
gctgcatgtg tcagaggttt tcacagtcat cacagaaact ggctagacta      1850
aagggcctag tgatactcct attttttatag gttaatgtca tgataataat      1900
ggtttcttag aagtcaggtg gcacttttct gggaaatgtg ctctgaaccc      1950
ctatttgttt attttttctaa atacattcaa atatgtatca gctcatgaga      2000
caataaccct gataaatgct tcaataatcc tcagtaatac aagggggtgtt      2050
agagctcaat gagccatatt caaagggaaa cttcttgctc taggccaaga      2100
ttaaattcca acatggatgc tgatttatat gggtataaat gggctagaga      2150
taatgttggg caatcaggtg caacaatcta tagattgtat gggaagccag      2200
atgctccaga gttgtttctg aaacatggca aaggtagtgt tgccaatgat      2250
gttacagatg agatggtcag actaaactgg ctgacagaat ttatgcctct      2300
tcctaccatc aagcatttta tcaggactcc tgatgatgca tggttactca      2350
ccactgctat ccctgggaaa acagcattcc aggtattaga agaatatcct      2400
gattcaggtg aaaatattgt tgatgctctg gcagtgttcc tgaggagatt      2450
gcattctatt cctgtttgta attgtccttt taacagtgat agagtattta      2500
gactggctca ggcacaatca agaatgaata atggtttggt tgatgctagt      2550
gattttgatg atgagaggaa tggctggcct gttgaacaag tctggaaaga      2600
aatgcataag cttttgccat tctcacagga ttcagttgtc actcatggtg      2650
atttctcact tgataacctt attttttgatg aggggaaatt aataggttgt      2700
attgatgttg gaagagttgg aatagcagac agataccagg atcttgccat      2750
cctatggaac tgccttggtg agttttctcc ttcattacag aagaggcttt      2800
ttcaaaaata tggtattgat aatcctgata tgaataaatt gcagtttcat      2850
ttgatgctgg atgagttttt ctaatcagaa ttggttaatt ggttgtaaca      2900
ctggcaacca gtgagtgtgg gtcttgcagt atcattgcag cactgggggcc      2950
agatggtaag ccctcctgta tcatagaggt accaaaacct taaaaccttt      3000
aaaagcctta tatattcttt tttttcttat aaaacttaaa accttagagg      3050
ctatttaagt tgctgattta tattaatttt attgttcaaa catgagagct      3100
tagtacatga aacatgagag cttagtacat tagccatgag agcttagtac      3150
attagccatg agggtttagt tcattaaaca tgagagctta gtacattaaa      3200
catgagagct tagtacatac tatcaacagg ttgaactgct gatgcatgc       3249
```

<210> SEQ ID NO 24
<211> LENGTH: 3378
<212> TYPE: DNA
<213> ORGANISM: artificial sequence
<220> FEATURE:
<223> OTHER INFORMATION: plasmid p80716-B6.1

<400> SEQUENCE: 24

| | | |
|---|---|---|
| gcatgccacc taggtctagc tttttttaat tttcaaaaat catacaatta | 50 |
| cccattcata caatcctctc catttcaact aaactacttc accttctact | 100 |
| agacttactc ttgtcttcct aatccaatat acctaaatat tcactttcta | 150 |
| taataaccct ctataaaata atcttaacct ctcccaaaac ttaataacaa | 200 |
| ttttctccaa atctctcact cctaccactt tcacatctac attccaccac | 250 |
| acttcccctc ataattaaac ctaactaact ttaccactat caacatacat | 300 |
| tcacccccca ccctcaacca cctaccatac tcatttaaca tactactcac | 350 |
| cacttcccta aacacatatc actcatcaat ttatttttt caccaagagg | 400 |
| atctttctta attaagggac cttccccagc ccccagggcc ctcagagtgg | 450 |
| acatggttgg ggaggccttt gggacaggtg cagttcccag agtctcagac | 500 |
| acacacatcc acccaccagt gaacactgtg accctcaccc caccccatcc | 550 |
| cctccagtgg gcaactgggt tgggtcagga ggggaaaacc ccctagggag | 600 |
| acactccata tactgcccag accaagttac ctgggaccag gccaaccctc | 650 |
| tccttctttg gtcaacccag gggaccctgg caggggccca ggactcaaac | 700 |
| cagtcaaggg aggggggtct agtgcccaac acccaaatat ggctcaagaa | 750 |
| gggcagcaac attcctgctg ggtggcccag agggaatgcc cccaggttat | 800 |
| ataaaacctg accagaggga caagctgcca ccaaaggtgg gatccccatg | 850 |
| ccactctggg tgttcttctt tgtgatcctc accctcagca acagctccca | 900 |
| ctgctcccca cctcccccct tgaccctcag gatgaggaga tatgcagatg | 950 |
| ccatcttcac caacagctac aggaaggttc tgggccagct gtctgccagg | 1000 |
| aagctgctcc aggacatcat gagcaggcag cagggagaga gcaaccaaga | 1050 |
| gagaggagca agggcaagac ttggtaggca agtagacagc atgtgggcag | 1100 |
| aacaaaagca aatggaattg gagagcatcc tggtggccct gctgcagaag | 1150 |
| cacagcagga actcccaggg atgaagattc ctcctgtgac cagggaattc | 1200 |
| ctgtagccaa aatgcaactg gatccagtta atcctctcat ttctgaccca | 1250 |
| ctttttcctt tgaaaataca ataaaattcc cccatacagg tgtgcattta | 1300 |
| aagcccatgg ctccaatttt ttaataacac caccctcat ctaccccaaa | 1350 |
| ctactgagaa tctaattata tctacattca cttacatatc catctccacc | 1400 |
| ctccctcaat agtctctaca ccagatgttg tcttatattg tttacctttc | 1450 |
| atacactttc atatcttaca acctttccat cctatccaaa caaattatca | 1500 |
| caccatctaa ctaacactga tagaaccaat acttatcact tctcactcat | 1550 |
| acaaaccaat tccaacaaaa aaccaccatc acacctacca atccctaaca | 1600 |
| tacccccctc aatctaatat attctttaat ataactttaa atatcccaaa | 1650 |
| tactccttcc ttatacccta aacagtgtta atagtcatct gtcccacctt | 1700 |
| ttttttcccat actagtcacc ctccaacacc agctgactct ccctgactgg | 1750 |

| | |
|---|---|
| cttgtctgct ccaggcatca gcttacagac aagctgtgaa gtctcctgga | 1800 |
| gctgcatgtg tcagaggttt tcacagtcat cacagaaact ggctagacta | 1850 |
| aagggcctag tgatactcct attttatag gttaatgtca tgataataat | 1900 |
| ggtttcttag aagtcaggtg gcacttttct gggaaatgtg ctctgaaccc | 1950 |
| ctatttgttt attttctaa atacattcaa atatgtatca gctcatgaga | 2000 |
| caataaccct gataaatgct tcaataatcc tcagtaatac aagggtgtt | 2050 |
| aggtaccaat gagccatatt caaagggaaa cttcttgctc taggccaaga | 2100 |
| ttaaattcca acatggatgc tgatttatat gggtataaat gggctagaga | 2150 |
| taatgttggg caatcaggtg caacaatcta tagattgtat gggaagccag | 2200 |
| atgctccaga gttgtttctg aaacatggca aaggtagtgt tgccaatgat | 2250 |
| gttacagatg agatggtcag actaaactgg ctgacagaat ttatgcctct | 2300 |
| tcctaccatc aagcatttta tcaggactcc tgatgatgca tggttactca | 2350 |
| ccactgctat ccctgggaaa acagcattcc aggtattaga agaatatcct | 2400 |
| gattcaggtg aaaatattgt tgatgctctg gcagtgttcc tgaggagatt | 2450 |
| gcattctatt cctgtttgta attgtccttt taacagtgat agagtattta | 2500 |
| gactggctca ggcacaatca agaatgaata atggtttggt tgatgctagt | 2550 |
| gattttgatg atgagaggaa tggctggcct gttgaacaag tctggaaaga | 2600 |
| aatgcataag ctttttgccat tctcacagga ttcagttgtc actcatggtg | 2650 |
| atttctcact tgataacctt attttgatg aggggaaatt aataggttgt | 2700 |
| attgatgttg gaagagttgg aatagcagac agataccagg atcttgccat | 2750 |
| cctatggaac tgccttggtg agttttctcc ttcattacag aagaggcttt | 2800 |
| ttcaaaaata tggtattgat aatcctgata tgaataaatt gcagtttcat | 2850 |
| ttgatgctgg atgagttttt ctaatcagaa ttggttaatt ggttgtaaca | 2900 |
| ctggcaacca gtgagtgtgg gtcttgcagt atcattgcag cactggggcc | 2950 |
| agatggtaag ccctcctgta tcatagagag ctcaccatgt cagcagttaa | 3000 |
| gtgttcctgt gtcactcaaa attgctttga gaggctctaa gggcttctca | 3050 |
| gtgagttaca tccctggctt gttgtccaca acagttaaac cttaaaagct | 3100 |
| ttaaaagcct tatatattct tttttttctt ataaaactta aaaccttaga | 3150 |
| ggctatttaa gttgctgatt tatattaatt ttattgttca aacatgagag | 3200 |
| cttagtaagt gaaacatgag agcttagtaa gttagccatg agagcttagt | 3250 |
| aagttagcca tgagggttta gttagttaaa catgagagct tagtaagtta | 3300 |
| aacatgagag cttagtaagt gaaacatgag agcttagtaa gtactatcaa | 3350 |
| caggttgaac tgctgatctt cagcatgc | 3378 |

<210> SEQ ID NO 25
<211> LENGTH: 3610
<212> TYPE: DNA
<213> ORGANISM: artificial sequence
<220> FEATURE:
<223> OTHER INFORMATION: plasmid p80717-B7.1

<400> SEQUENCE: 25

| | |
|---|---|
| gcatgccacc taggtctagc tttttttaat tttcaaaaat catacaatta | 50 |
| cccattcata caatcctctc catttcaact aaactacttc accttctact | 100 |

```
agacttactc ttgtcttcct aatccaatat acctaaatat tcactttcta          150
taataaccct ctataaaata atcttaacct ctcccaaaac ttaataacaa          200 tttctccaa atctctcact cctaccactt tcacatctac attccaccac           250
acttcccctc ataattaaac ctaactaact ttaccactat caacatacat          300 tcaccccca ccctcaacca cctaccatac tcatttaaca tactactcac           350
cacttcccta aacacatatc actcatcaat ttatttttt caccaagagg           400 atctttctta attaagggac cttccccagc cccagggcc ctcagagtgg           450 acatggttgg ggaggccttt gggacaggtg cagttcccag agtctcagac          500
acacacatcc acccaccagt gaacactgtg accctcaccc caccccatcc          550
cctccagtgg gcaactgggt tgggtcagga ggggaaaacc ccctagggag          600
acactccata tactgcccag accaagttac ctgggaccag gccaaccctc          650
tccttctttg gtcaacccag gggacccctgg caggggccca ggactcaaac         700
cagtcaaggg aggggggtct agtgcccaac acccaaatat ggctcaagaa          750
gggcagcaac attcctgctg gtggcccag agggaatgcc cccaggttat           800
ataaaacctg accagaggga caagctgcca ccaaaggtgg gatccccatg          850
ccactctggg tgttcttctt tgtgatcctc accctcagca acagctccca          900
ctgctcccca cctcccccctt tgaccctcag gatgaggaga tatgcagatg         950
ccatcttcac caacagctac aggaaggttc tgggccagct gtctgccagg          1000
aagctgctcc aggacatcat gagcaggcag cagggagaga gcaaccaaga          1050
gagaggagca agggcaagac ttggtaggca agtagacagc atgtgggcag          1100
aacaaaagca aatggaattg gagagcatcc tggtggccct gctgcagaag          1150
cacagcagga actcccaggg atgaagattc ctcctgtgac cagggaattc          1200
ctgtagccaa aatgcaactg gatccagtta atcctctcat ttctgaccca          1250 cttttctt tgaaaataca ataaaattcc cccatacagg tgtgcattta            1300
aagcccatgg ctccaatttt ttaataacac caccccctcat ctaccccaaa         1350 ctactgagaa tctaattata tctacattca cttacatatc catctccacc          1400
ctccctcaat agtctctaca ccagatgttg tcttatattg tttaccttc           1450 atacactttc atatcttaca acctttccat cctatccaaa caattatca           1500 caccatctaa ctaacactga tagaaccaat acttatcact tctcactcat          1550
acaaaccaat tccaacaaaa aaccaccatc acacctacca atccctaaca          1600
tacccccctc aatctaatat attctttaat ataactttaa atatcccaaa          1650
tactccttcc ttatacccta aacagtgtta atagtcatct gtcccacctt          1700
tttttcccat actagtcacc ctccaacacc agctgactct ccctgactgg          1750
cttgtctgct ccaggcatca gcttacagac aagctgtgaa gtctcctgga          1800
gctgcatgtg tcagaggttt tcacagtcat cacagaaact ggctagacta          1850
aagggcctag tgatactcct attttatag gttaatgtca tgataataat           1900
ggtttcttag aagtcaggtg gcacttttct gggaaatgtg ctctgaaccc          1950
ctatttgttt attttttctaa atacattcaa atatgtatca gctcatgaga         2000
caataaccct gataaatgct tcaataatcc tcagtaatac aagggggtgtt         2050
```

-continued

```
aggtaccaat gagccatatt caaagggaaa cttcttgctc taggccaaga          2100
ttaaattcca acatggatgc tgatttatat gggtataaat gggctagaga          2150
taatgttggg caatcaggtg caacaatcta tagattgtat gggaagccag          2200
atgctccaga gttgtttctg aaacatggca aaggtagtgt tgccaatgat          2250
gttacagatg agatggtcag actaaactgg ctgacagaat ttatgcctct          2300
tcctaccatc aagcatttta tcaggactcc tgatgatgca tggttactca          2350
ccactgctat ccctgggaaa acagcattcc aggtattaga agaatatcct          2400
gattcaggtg aaaatattgt tgatgctctg gcagtgttcc tgaggagatt          2450
gcattctatt cctgtttgta attgtccttt taacagtgat agagtattta          2500
gactggctca ggcacaatca agaatgaata atggtttggt tgatgctagt          2550
gattttgatg atgagaggaa tggctggcct gttgaacaag tctggaaaga          2600
aatgcataag cttttgccat tctcacagga ttcagttgtc actcatggtg          2650
atttctcact tgataacctt attttgatg aggggaaatt aataggttgt           2700
attgatgttg aagagttgg aatagcagac agataccagg atcttgccat           2750
cctatggaac tgccttggtg agtttctcc ttcattacag aagaggcttt           2800
ttcaaaaata tggtattgat aatcctgata tgaataaatt gcagtttcat          2850
ttgatgctgg atgagttttt ctaatcagaa ttggttaatt ggttgtaaca          2900
ctggcaacca gtgagtgtgg gtcttgcagt atcattgcag cactggggcc          2950
agatggtaag ccctcctgta tcatagagag ctcaagatca aaggatcttc          3000
ttgagatcct tttttctgc gcgtaatctg ctgcttgcaa acaaaaaaac           3050
caccgctacc agcggtggtt tgtttgccgg atcaagagct accaactctt          3100
tttccgaagg taactggctt cagcagagcg cagataccaa atactgtcct          3150
tctagtgtag ccgtagttag gccaccactt caagaactct gtagcaccgc          3200
ctacatacct cgctctgcta atcctgttac cagtggctgc tgccagtggc          3250
gataagtcgt gtcttaccgg gttggactca agacgatagt taccggataa          3300
ggcgcagcgg tcgggctgaa cggggggttc gtgcacacag cccagcttgg          3350
agcgaacgac ctacaccgaa ctgagatacc tacagcgtga gctatgagaa          3400
agcgccacgc ttcccgaagg agaaaggcg gacaggtatc cggtaagcgg           3450
cagggtcgga acaggagagc gcacgaggga gcttccaggg ggaaacgcct          3500
ggtatcttta tagtcctgtc gggtttcgcc acctctgact tgagcgtcga          3550
tttttgtgat gctcgtcagg ggggcggagc ctatggaaaa acgccagcaa          3600
cgcggcatgc                                                     3610
```

<210> SEQ ID NO 26
<211> LENGTH: 3612
<212> TYPE: DNA
<213> ORGANISM: artificial sequence
<220> FEATURE:
<223> OTHER INFORMATION: plasmid p80718-B8.1

<400> SEQUENCE: 26

```
gcatgccacc taggtctagc ttttttttaat tttcaaaaat catacaatta           50
cccattcata caatcctctc catttcaact aaactactc accttctact             100
agacttactc ttgtcttcct aatccaatat acctaaatat tcactttcta            150
```

-continued

```
taataaccct ctataaaata atcttaacct ctcccaaaac ttaataacaa        200
ttttctccaa atctctcact cctaccactt tcacatctac attccaccac        250
acttcccctc ataattaaac ctaactaact ttaccactat caacatacat        300 tcaccccca  ccctcaacca cctaccatac tcatttaaca tactactcac        350
cacttcccta aacacatatc actcatcaat ttattttttt caccaagagg        400
atctttctta attaagggac cttccccagc ccccagggcc ctcagagtgg        450
acatggttgg ggaggccttt gggacaggtg cagttcccag agtctcagac        500
acacacatcc ccccaccagt gaacactgtg accctcaccc caccccatcc        550
cctccagtgg gcaactgggt tgggtcagga ggggaaaacc ccctagggag        600
acactccata tactgcccag accaagttac ctgggaccag gccaaccctc        650
tccttctttg gtcaacccag gggaccctgg caggggccca ggactcaaac        700
cagtcaaggg agggggtct  agtgcccaac acccaaatat ggctcaagaa        750
gggcagcaac attcctgctg ggtggcccag agggaatgcc cccaggttat        800
ataaaacctg accagaggga caagctgcca ccaaaggtgg gatccccatg        850
ccactctggg tgttcttctt tgtgatcctc accctcagca acagctccca        900
ctgctcccca cctcccccctt tgaccctcag gatgaggaga tatgcagatg       950
ccatcttcac caacagctac aggaaggttc tgggccagct gtctgccagg       1000
aagctgctcc aggacatcat gagcaggcag cagggagaga gcaaccaaga       1050
gagaggagca agggcaagac ttggtaggca agtagacagc atgtgggcag       1100
aacaaaagca aatggaattg gagagcatcc tggtggccct gctgcagaag       1150
cacagcagga actcccaggg atgaagattc ctcctgtgac cagggaattc       1200
ctgtagccaa aatgcaactg atccagtta  atcctctcat ttctgaccca       1250 cttttttcctt tgaaaataca ataaaattcc cccatacagg tgtgcattta       1300
aagcccatgg ctccaatttt ttaataacac caccccctcat ctaccccaaa      1350 ctactgagaa tctaattata tctacattca cttacatatc catctccacc       1400
ctccctcaat agtctctaca ccagatgttg tcttatattg tttaccttc        1450 atacactttc atatcttaca acctttccat cctatccaaa caattatca        1500 caccatctaa ctaacactga tagaaccaat acttatcact tctcactcat       1550
acaaaccaat tccaacaaaa aaccaccatc acacctacca atccctaaca       1600
tacccccctc aatctaatat attctttaat ataactttaa atatcccaaa       1650
tactccttcc ttatacccta aacagtgtta atagtcatct gtcccacctt       1700
tttttcccat actagtcacc ctccaacacc agctgactct ccctgactgg       1750
cttgtctgct ccaggcatca gcttacagac aagctgtgaa gtctcctgga       1800
gctgcatgtg tcagaggttt tcacagtcat cacagaaact ggctagacta       1850
aagggcctag tgatactcct attttttatag gttaatgtca tgataataat       1900
ggtttcttag aagtcaggtg gcacttttct gggaaatgtg ctctgaaccc       1950
ctatttgttt attttttctaa atacattcaa atatgtatca gctcatgaga       2000
caataaccct gataaatgct tcaataatcc tcagtaatac aagggtgtt        2050 aggtaccaat gagccatatt caagggaaa  cttcttgctc taggccaaga       2100
```

```
ttaaattcca acatggatgc tgatttatat gggtataaat gggctagaga        2150
taatgttggg caatcaggtg caacaatcta tagattgtat gggaagccag        2200
atgctccaga gttgtttctg aaacatggca aggtagtgt tgccaatgat         2250
gttacagatg agatggtcag actaaactgg ctgacagaat ttatgcctct        2300
tcctaccatc aagcatttta tcaggactcc tgatgatgca tggttactca        2350
ccactgctat ccctgggaaa acagcattcc aggtattaga agaatatcct        2400
gattcaggtg aaaatattgt tgatgctctg gcagtgttcc tgaggagatt        2450
gcattctatt cctgttttgta attgtccttt taacagtgat agagtattta       2500
gactggctca ggcacaatca agaatgaata atggtttggt tgatgctagt        2550
gattttgatg atgagaggaa tggctggcct gttgaacaag tctggaaaga        2600
aatgcataag cttttgccat tctcacagga ttcagttgtc actcatggtg        2650
atttctcact tgataacctt atttttgatg aggggaaatt aataggttgt        2700
attgatgttg gaagagttgg aatagcagac agataccagg atcttgccat        2750
cctatggaac tgccttggtg agttttctcc ttcattacag aagaggcttt        2800
ttcaaaaata tggtattgat aatcctgata tgaataaatt gcagtttcat        2850
ttgatgctgg atgagttttt ctaatcagaa ttggttaatt ggttgtaaca        2900
ctggcaacca gtgagtgtgg gtcttgcagt atcattgcag cactgggggcc       2950
agatggtaag ccctccttgg gatcccacag agctcaagat caaaggatct        3000
tcttgagatc cttttttttct gagagtaatc tgctgcttgc aaacaaaaaa       3050
accacagcta ccagaggtgg tttgtttgca ggatcaagag ctaccaactc        3100
ttttttcagaa ggtaactggc ttcagcgag agcagatacc aaatactgtc        3150
cttctagtgt agcagtagtt aggccaccac ttcaagaact ctgtagcaca        3200
gcctacatac ctagctctgc taatcctgtt accagtggct gctgccagtg        3250
gagataagta gtgtcttaca gggttggact caagaagata gttacaggat        3300
aaggagcaga ggtagggctg aaaggggggt tagtgcacac agcccagctt        3350
ggagagaaag acctacacag aactgagata cctacagagt gagctatgag        3400
aaagagccaa gcttccagaa gggagaaagg aggacaggta tcaggtaaga        3450
ggcagggtag gaacaggaga gagcaagagg gagcttccag gggggaaaagc       3500
ctggtatctt tatagtcctg tagggtttag ccacctctga cttgagagta        3550
gattttttgtg atgctagtca gggggggagga gcctatggaa aaaagccagc      3600
aaagaggcat gc                                                 3612
```

<210> SEQ ID NO 27
<211> LENGTH: 3690
<212> TYPE: DNA
<213> ORGANISM: artificial sequence
<220> FEATURE:
<223> OTHER INFORMATION: plasmid p80715-5.2

<400> SEQUENCE: 27

```
gcatgccacc taggtctcag ttttttcatgt ttttcatgtt tttcatgttt        50
ttcacatcag ttttttcatgt tttcatgtt tttcatgttt ttcacatcag       100
ttttttcatgt tttcatgtt tttcatgttt ttcacatcag ttttttcatgt     150
ttttcatgtt tttcatgttt ttcacatcag ttttttcatgt ttttcatgtt     200
```

```
tttcatgttt ttcacatcag tttttcatgt ttttcatgtt tttcatgttt      250
ttcacatcag tttttcatgt ttttcatgtt tttcatgttt ttcacatcag      300
tttttcatgt ttttcatgtt tttcatgttt ttcacatcag tttttcatgt      350
ttttcatgtt tttcatgttt ttcacatcag tttttcatgt ttttcatgtt      400
tttcatgttt ttcacatcag tttttcatgt ttttcatgtt tttcatgttt      450
ttcacatcag tttttcatgt ttttcatgtt tttcatgttt ttcacatcag      500
tttttcatgt ttttcatgtt tttcatgttt ttcacatcag tttttcatgt      550
ttttcatgtt tttcatgttt ttcacatcag tttttcatgt ttttcatgtt      600
tttcatgttt ttcacatcag tttttcatgt ttttcatgtt tttcatgttt      650
ttcacatcag tttttcatgt ttttcatgtt tttcatgttt ttcacatcag      700
tttttcatgt ttttcatgtt tttcatgttt ttcacatcag tttttcatgt      750
ttttcatgtt tttcatgttt ttcacatcag tttttcatgt ttttcatgtt      800
tttcatgttt ttcacatcag tttttcatgt ttttcatgtt tttcatgttt      850
ttttaaggga ccttccccag cccccagggc cctcagagtg gacatggttg      900
gggaggcctt tgggacaggt gcagttccca gagtctcaga cacacacatc      950
cacccaccag tgaacactgt gaccctcacc ccaccccatc ccctccagtg     1000
ggcaactggg ttgggtcagg aggggaaaac cccctaggga gacactccat     1050
atactgccca gaccaagtta cctgggacca ggccaaccct ctccttcttt     1100
ggtcaaccca ggggaccctg gcaggggccc aggactcaaa ccagtcaagg     1150
gagggggtc tagtgcccaa cacccaaata tggctcaaga agggcagcaa      1200
cattcctgct gggtggccca gagggaatgc ccccaggtta tataaaacct     1250
gaccagaggg acaagctgcc accaaaggtg ggatccccat gccactctgg     1300
gtgttcttct ttgtgatcct caccctcagc aacagctccc actgctcccc     1350
acctcccct ttgaccctca ggatgaggag atatgcagat gccatcttca      1400
ccaacagcta caggaaggtt ctgggccagc tgtctgccag gaagctgctc     1450
caggacatca tgagcaggca gcagggagag agcaaccaag agagaggagc     1500
aagggcaaga cttggtaggc aagtagacag catgtgggca gaacaaaagc     1550
aaatggaatt ggagagcatc ctggtggccc tgctgcagaa gcacagcagg     1600
aactcccagg gatgaagatt cctcctgtga ccagggaatt cctgtagcca     1650
aaatgcaact ggatccagtt aatcctctca tttctgaccc acttttttcct    1700
ttgaaaatac aataaaattc ccccatacag gtgtgcattt aaagcccatg     1750
gctccaattt tttaataaca ccaccctca tctaccccaa actactgaga      1800
atctaattat atctacattc acttacatat ccatctccac cctccctcaa     1850
tagtctctac accagatgtt gtcttatatt gtttacctttt catacacttt    1900
catatcttac aaccttttcca tcctatccaa acaaattatc acaccatcta    1950
actaacactg atagaaccaa tacttatcac ttctcactca tacaaaccaa     2000
ttccaacaaa aaaccaccat cacacctacc aatccctaac atacccccct     2050
caatctaata tattctttaa tataacttta aatatcccaa atactccttc     2100
cttataccct aaacagtgtt aatagtcatc tgtcccacct ttttttccca     2150
```

```
tactagtcac cctccaacac cagctgactc tccctgactg gcttgtctgc         2200
tccaggcatc agcttacaga caagctgtga agtctcctgg agctgcatgt         2250
gtcagaggtt ttcacagtca tcacagaaac tggctagact aaagggccta         2300
gtgatactcc tattttata ggttaatgtc atgataataa tggtttctta          2350
gaagtcaggt ggcactttc tgggaaatgt gctctgaacc cctatttgtt          2400 tattttcta aatacattca aatatgtatc agctcatgag acaataaccc          2450
tgataaatgc ttcaataatc ctcagtaata caaggggtgt tagagctcaa         2500
tgagccatat tcaaagggaa acttcttgct ctaggccaag attaaattcc         2550
aacatggatg ctgatttata tgggtataaa tgggctagag ataatgttgg         2600
gcaatcaggt gcaacaatct atagattgta tgggaagcca gatgctccag         2650
agttgtttct gaaacatggc aaaggtagtg ttgccaatga tgttacagat         2700
gagatggtca gactaaactg gctgacagaa tttatgcctc ttcctaccat         2750
caagcatttt atcaggactc ctgatgatgc atggttactc accactgcta         2800
tccctgggaa aacagcattc caggtattag aagaatatcc tgattcaggt         2850
gaaaatattg ttgatgctct ggcagtgttc ctgaggagat tgcattctat         2900
tcctgtttgt aattgtcctt ttaacagtga tagagtattt agactggctc         2950
aggcacaatc aagaatgaat aatggttttgg ttgatgctag tgattttgat        3000
gatgagagga atggctggcc tgttgaacaa gtctggaaag aaatgcataa         3050
gcttttgcca ttctcacagg attcagttgt cactcatggt gatttctcac         3100 ttgataaccct tattttgat gaggggaaat taataggtttg tattgatgtt        3150 ggaagagttg gaatagcaga cagataccag gatcttgcca tcctatggaa         3200
ctgccttggt gagttttctc cttcattaca gaagaggctt tttcaaaaat         3250
atggtattga taatcctgat atgaataaat tgcagtttca tttgatgctg         3300
gatgagtttt tctaatcaga attggttaat tggttgtaac actggcaacc         3350
agtgagtgtg ggtcttgcag tatcattgca gcactgggc cagatggtaa          3400 gccctcctgt atcatagagg taccaaaacc ttaaaaccttt taaaagcctt        3450 atatattctt ttttttctta taaaacttaa aaccttagag gctatttaag         3500
ttgctgattt atattaattt tattgttcaa acatgagagc ttagtacatg         3550
aaacatgaga gcttagtaca ttagccatga gagcttagta cattagccat         3600 gagggttag ttcattaaac atgagagctt agtacattaa acatgagagc          3650
ttagtacata ctatcaacag gttgaactgc tgatgcatgc                    3690
```

<210> SEQ ID NO 28
<211> LENGTH: 3819
<212> TYPE: DNA
<213> ORGANISM: artificial sequence
<220> FEATURE:
<223> OTHER INFORMATION: plasmid p80716-B6.2

<400> SEQUENCE: 28

```
gcatgccacc taggtctcag ttttcatgt ttttcatgtt tttcatgttt           50
ttcacatcag ttttcatgt ttttcatgtt tttcatgttt ttcacatcag          100 ttttcatgt ttttcatgtt tttcatgttt ttcacatcag ttttcatgt           150 ttttcatgtt tttcatgttt ttcacatcag ttttcatgt ttttcatgtt          200
```

```
tttcatgttt ttcacatcag tttttcatgt ttttcatgtt tttcatgttt      250
ttcacatcag tttttcatgt ttttcatgtt tttcatgttt ttcacatcag      300
tttttcatgt ttttcatgtt tttcatgttt ttcacatcag tttttcatgt      350
ttttcatgtt tttcatgttt ttcacatcag tttttcatgt ttttcatgtt      400
tttcatgttt ttcacatcag tttttcatgt ttttcatgtt tttcatgttt      450
ttcacatcag tttttcatgt ttttcatgtt tttcatgttt ttcacatcag      500
tttttcatgt ttttcatgtt tttcatgttt ttcacatcag tttttcatgt      550
ttttcatgtt tttcatgttt ttcacatcag tttttcatgt ttttcatgtt      600
tttcatgttt ttcacatcag tttttcatgt ttttcatgtt tttcatgttt      650
ttcacatcag tttttcatgt ttttcatgtt tttcatgttt ttcacatcag      700
tttttcatgt ttttcatgtt tttcatgttt ttcacatcag tttttcatgt      750
ttttcatgtt tttcatgttt ttcacatcag tttttcatgt ttttcatgtt      800
tttcatgttt ttcacatcag tttttcatgt ttttcatgtt tttcatgttt      850
ttttaaggga ccttccccag cccccagggc cctcagagtg gacatggttg      900
gggaggcctt tgggacaggt gcagttccca gagtctcaga cacacacatc      950
cacccaccag tgaacactgt gaccctcacc ccaccccatc ccctccagtg     1000
ggcaactggg ttgggtcagg aggggaaaac cccctaggga gacactccat     1050
atactgccca gaccaagtta cctgggacca ggccaaccct ctccttcttt     1100
ggtcaaccca ggggaccctg gcaggggccc aggactcaaa ccagtcaagg     1150
gaggggggtc tagtgcccaa cacccaaata tggctcaaga agggcagcaa     1200
cattcctgct gggtggccca gagggaatgc ccccaggtta tataaaacct     1250
gaccagaggg acaagctgcc accaaaggtg ggatccccat gccactctgg     1300
gtgttcttct ttgtgatcct caccctcagc aacagctccc actgctcccc     1350 acctcccccct ttgaccctca ggatgaggag atatgcagat gccatcttca     1400
ccaacagcta caggaaggtt ctgggccagc tgtctgccag gaagctgctc     1450
caggacatca tgagcaggca gcagggagag agcaaccaag agagaggagc     1500
aagggcaaga cttggtaggc aagtagacag catgtgggca gaacaaaagc     1550
aaatggaatt ggagagcatc ctggtggccc tgctgcagaa gcacagcagg     1600
aactcccagg gatgaagatt cctcctgtga ccagggaatt cctgtagcca     1650
aaatgcaact ggatccagtt aatcctctca tttctgaccc acttttttcct    1700 ttgaaaatac aataaaattc ccccatacag gtgtgcattt aaagcccatg     1750
gctccaattt tttaataaca ccaccccctca tctaccccaa actactgaga    1800
atctaattat atctacattc acttacatat ccatctccac cctccctcaa     1850
tagtctctac accagatgtt gtcttatatt gtttacctttt catacacttt    1900 catatcttac aacctttcca tcctatccaa acaaattatc acaccatcta     1950
actaacactg atagaaccaa tacttatcac ttctcactca tacaaaccaa     2000
ttccaacaaa aaaccaccat cacacctacc aatccctaac ataccccct     2050 caatctaata tattctttaa tataacttta aatatcccaa atactccttc     2100
cttataccct aaacagtgtt aatagtcatc tgtcccacct tttttttccca    2150
```

| | |
|---|---|
| tactagtcac cctccaacac cagctgactc tccctgactg gcttgtctgc | 2200 |
| tccaggcatc agcttacaga caagctgtga agtctcctgg agctgcatgt | 2250 |
| gtcagaggtt ttcacagtca tcacagaaac tggctagact aaagggccta | 2300 |
| gtgatactcc tattttata ggttaatgtc atgataataa tggtttctta | 2350 |
| gaagtcaggt ggcacttttc tgggaaatgt gctctgaacc cctatttgtt | 2400 |
| tattttcta aatacattca aatatgtatc agctcatgag acaataaccc | 2450 |
| tgataaatgc ttcaataatc ctcagtaata caaggggtgt taggtaccaa | 2500 |
| tgagccatat tcaaagggaa acttcttgct ctaggccaag attaaattcc | 2550 |
| aacatggatg ctgatttata tgggtataaa tgggctagag ataatgttgg | 2600 |
| gcaatcaggt gcaacaatct atagattgta tgggaagcca gatgctccag | 2650 |
| agttgtttct gaaacatggc aaaggtagtg ttgccaatga tgttacagat | 2700 |
| gagatggtca gactaaactg gctgacagaa tttatgcctc ttcctaccat | 2750 |
| caagcatttt atcaggactc ctgatgatgc atggttactc accactgcta | 2800 |
| tccctgggaa aacagcattc caggtattag aagaatatcc tgattcaggt | 2850 |
| gaaaatattg ttgatgctct ggcagtgttc ctgaggagat tgcattctat | 2900 |
| tcctgtttgt aattgtcctt ttaacagtga tagagtattt agactggctc | 2950 |
| aggcacaatc aagaatgaat aatggtttgg ttgatgctag tgattttgat | 3000 |
| gatgagagga atggctggcc tgttgaacaa gtctggaaag aaatgcataa | 3050 |
| gcttttgcca ttctcacagg attcagttgt cactcatggt gatttctcac | 3100 |
| ttgataacct tatttttgat gagggaaat taataggttg tattgatgtt | 3150 |
| ggaagagttg gaatagcaga cagataccag gatcttgcca tcctatggaa | 3200 |
| ctgccttggt gagttttctc cttcattaca gaagaggctt tttcaaaaat | 3250 |
| atggtattga taatcctgat atgaataaat tgcagtttca tttgatgctg | 3300 |
| gatgagtttt tctaatcaga attggttaat tggttgtaac actggcaacc | 3350 |
| agtgagtgtg ggtcttgcag tatcattgca gcactgggc cagatggtaa | 3400 |
| gccctcctgt atcatagaga gctcaccatg tcagcagtta agtgttcctg | 3450 |
| tgtcactcaa aattgctttg agaggctcta agggcttctc agtgagttac | 3500 |
| atccctggct tgttgtccac aacagttaaa ccttaaaagc tttaaaagcc | 3550 |
| ttatatattc tttttttct tataaaactt aaaaccttag aggctattta | 3600 |
| agttgctgat ttatattaat tttattgttc aaacatgaga gcttagtaag | 3650 |
| tgaaacatga gagcttagta agttagccat gagagcttag taagttagcc | 3700 |
| atgagggttt agttagttaa acatgagagc ttagtaagtt aaacatgaga | 3750 |
| gcttagtaag tgaaacatga gagcttagta agtactatca acaggttgaa | 3800 |
| ctgctgatct tcagcatgc | 3819 |

<210> SEQ ID NO 29
<211> LENGTH: 4051
<212> TYPE: DNA
<213> ORGANISM: artificial sequence
<220> FEATURE:
<223> OTHER INFORMATION: plasmid p80717-B7.2

<400> SEQUENCE: 29

| | |
|---|---|
| gcatgccacc taggtctcag ttttcatgt ttttcatgtt tttcatgttt | 50 |

```
ttcacatcag ttttcatgt tttcatgtt tttcatgttt ttcacatcag      100
tttttcatgt ttttcatgtt tttcatgttt ttcacatcag tttttcatgt    150
ttttcatgtt tttcatgttt ttcacatcag tttttcatgt ttttcatgtt    200
tttcatgttt ttcacatcag tttttcatgt ttttcatgtt tttcatgttt    250
ttcacatcag tttttcatgt ttttcatgtt tttcatgttt ttcacatcag    300
tttttcatgt ttttcatgtt tttcatgttt ttcacatcag tttttcatgt    350
ttttcatgtt tttcatgttt ttcacatcag tttttcatgt ttttcatgtt    400
tttcatgttt ttcacatcag tttttcatgt ttttcatgtt tttcatgttt    450
ttcacatcag tttttcatgt ttttcatgtt tttcatgttt ttcacatcag    500
tttttcatgt ttttcatgtt tttcatgttt ttcacatcag tttttcatgt    550
ttttcatgtt tttcatgttt ttcacatcag tttttcatgt ttttcatgtt    600
tttcatgttt ttcacatcag tttttcatgt ttttcatgtt tttcatgttt    650
ttcacatcag tttttcatgt ttttcatgtt tttcatgttt ttcacatcag    700
tttttcatgt ttttcatgtt tttcatgttt ttcacatcag tttttcatgt    750
ttttcatgtt tttcatgttt ttcacatcag tttttcatgt ttttcatgtt    800
tttcatgttt ttcacatcag tttttcatgt ttttcatgtt tttcatgttt    850
ttttaaggga ccttccccag cccccagggc cctcagagtg gacatggttg    900
gggaggcctt tgggacaggt gcagttccca gagtctcaga cacacacatc    950
cacccaccag tgaacactgt gaccctcacc ccaccccatc ccctccagtg   1000
ggcaactggg ttgggtcagg aggggaaaac ccctaggga gacactccat    1050
atactgccca gaccaagtta cctgggacca ggccaaccct ctccttcttt   1100
ggtcaaccca ggggaccctg gcaggggccc aggactcaaa ccagtcaagg   1150
gagggggtc tagtgcccaa cacccaaata tggctcaaga agggcagcaa    1200
cattcctgct gggtggccca gagggaatgc ccccaggtta tataaaacct   1250
gaccagaggg acaagctgcc accaaaggtg ggatccccat gccactctgg   1300
gtgttcttct ttgtgatcct caccctcagc aacagctccc actgctcccc   1350
acctccccct ttgaccctca ggatgaggag atatgcagat gccatcttca   1400
ccaacagcta caggaaggtt ctgggccagc tgtctgccag gaagctgctc   1450
caggacatca tgagcaggca gcaggagag agcaaccaag agagaggagc    1500
aagggcaaga cttggtaggc aagtagacag catgtgggca gaacaaaagc   1550
aaatggaatt ggagagcatc ctggtggccc tgctgcagaa gcacagcagg   1600
aactcccagg gatgaagatt cctcctgtga ccagggaatt cctgtagcca   1650
aaatgcaact ggatccagtt aatcctctca tttctgaccc acttttttcct  1700
ttgaaaatac aataaaattc ccccatacag gtgtgcattt aaagcccatg   1750
gctccaattt tttaataaca ccaccCctca tctaccccaa actactgaga   1800
atctaattat atctacattc acttacatat ccatctccac cctccctcaa   1850
tagtctctac accagatgtt gtcttatatt gtttaccttt catacacttt   1900
catatcttac aaccttttcca tcctatccaa acaaattatc acaccatcta  1950
actaacactg atagaaccaa tacttatcac ttctcactca tacaaaccaa   2000
```

```
ttccaacaaa aaaccaccat cacacctacc aatccctaac ataccccct       2050
caatctaata tattctttaa tataacttta aatatcccaa atactccttc       2100
cttatacccct aaacagtgtt aatagtcatc tgtcccacct ttttttccca     2150
tactagtcac cctccaacac cagctgactc tccctgactg gcttgtctgc      2200
tccaggcatc agcttacaga caagctgtga agtctcctgg agctgcatgt      2250
gtcagaggtt tcacagtca tcacagaaac tggctagact aaagggccta       2300
gtgatactcc tattttata ggttaatgtc atgataataa tggtttctta       2350
gaagtcaggt ggcacttttc tgggaaatgt gctctgaacc cctatttgtt      2400
tattttcta aatacattca aatatgtatc agctcatgag acaataaccc       2450
tgataaatgc ttcaataatc ctcagtaata caagggtgt taggtaccaa       2500
tgagccatat tcaaagggaa acttcttgct ctaggccaag attaaattcc      2550
aacatggatg ctgatttata tgggtataaa tgggctagag ataatgttgg      2600
gcaatcaggt gcaacaatct atagattgta tgggaagcca gatgctccag      2650
agttgtttct gaaacatggc aaaggtagtg ttgccaatga tgttacagat      2700
gagatggtca gactaaactg gctgacagaa tttatgcctc ttcctaccat      2750
caagcatttt atcaggactc ctgatgatgc atggttactc accactgcta      2800
tccctgggaa aacagcattc caggtattag aagaatatcc tgattcaggt      2850
gaaaatattg ttgatgctct ggcagtgttc ctgaggagat tgcattctat      2900
tcctgttgt aattgtcctt ttaacagtga tagagtattt agactggctc       2950
aggcacaatc aagaatgaat aatggtttgg ttgatgctag tgattttgat      3000
gatgagagga atggctggcc tgttgaacaa gtctggaaag aaatgcataa      3050
gcttttgcca ttctcacagg attcagttgt cactcatggt gatttctcac      3100
ttgataacct tatttttgat gaggggaaat taataggttg tattgatgtt      3150
ggaagagttg gaatagcaga cagataccag gatcttgcca tcctatggaa      3200
ctgccttggt gagttttctc cttcattaca gaagaggctt tttcaaaaat      3250
atggtattga taatcctgat atgaataaat tgcagtttca tttgatgctg      3300
gatgagtttt tctaatcaga attggttaat tggttgtaac actggcaacc      3350
agtgagtgtg ggtcttgcag tatcattgca gcactggggc cagatggtaa      3400
gccctcctgt atcatagaga gctcaagatc aaaggatctt cttgagatcc      3450
ttttttctg cgcgtaatct gctgcttgca acaaaaaaa ccaccgctac        3500
cagcggtggt ttgtttgccg gatcaagagc taccaactct ttttccgaag      3550
gtaactggct tcagcagagc gcagatacca aatactgtcc ttctagtgta      3600
gccgtagtta ggccaccact tcaagaactc tgtagcaccg cctacatacc      3650
tcgctctgct aatcctgtta ccagtggctg ctgccagtgg cgataagtcg      3700
tgtcttaccg ggttggactc aagacgatag ttaccggata aggcgcagcg      3750
gtcgggctga acgggggtt cgtgcacaca gcccagcttg gagcgaacga       3800
cctacaccga actgagatac ctacagcgtg agctatgaga aagcgccacg      3850
cttcccgaag ggagaaaggc ggacaggtat ccggtaagcg gcagggtcgg      3900
aacaggagag cgcacgaggg agcttccagg gggaaacgcc tggtatcttt      3950
atagtcctgt cgggtttcgc cacctctgac ttgagcgtcg attttttgtga     4000
```

```
tgctcgtcag ggggcggag cctatggaaa aacgccagca acgcggcatg        4050
c                                                             4051

<210> SEQ ID NO 30
<211> LENGTH: 4053
<212> TYPE: DNA
<213> ORGANISM: artificial sequence
<220> FEATURE:
<223> OTHER INFORMATION: plasmid p80718-B8.2

<400> SEQUENCE: 30
gcatgccacc taggtctcag tttttcatgt ttttcatgtt tttcatgttt        50
ttcacatcag tttttcatgt ttttcatgtt tttcatgttt ttcacatcag        100
tttttcatgt ttttcatgtt tttcatgttt ttcacatcag tttttcatgt        150
ttttcatgtt tttcatgttt ttcacatcag tttttcatgt ttttcatgtt        200
tttcatgttt ttcacatcag tttttcatgt ttttcatgtt tttcatgttt        250
ttcacatcag tttttcatgt ttttcatgtt tttcatgttt ttcacatcag        300
tttttcatgt ttttcatgtt tttcatgttt ttcacatcag tttttcatgt        350
ttttcatgtt tttcatgttt ttcacatcag tttttcatgt ttttcatgtt        400
tttcatgttt ttcacatcag tttttcatgt ttttcatgtt tttcatgttt        450
ttcacatcag tttttcatgt ttttcatgtt tttcatgttt ttcacatcag        500
tttttcatgt ttttcatgtt tttcatgttt ttcacatcag tttttcatgt        550
ttttcatgtt tttcatgttt ttcacatcag tttttcatgt ttttcatgtt        600
tttcatgttt ttcacatcag tttttcatgt ttttcatgtt tttcatgttt        650
ttcacatcag tttttcatgt ttttcatgtt tttcatgttt ttcacatcag        700
tttttcatgt ttttcatgtt tttcatgttt ttcacatcag tttttcatgt        750
ttttcatgtt tttcatgttt ttcacatcag tttttcatgt ttttcatgtt        800
tttcatgttt ttcacatcag tttttcatgt ttttcatgtt tttcatgttt        850
ttttaaggga ccttccccag cccccagggc cctcagagtg acatggttg         900 gggaggcctt tgggacaggt gcagttccca gagtctcaga cacacacatc        950
cacccaccag tgaacactgt gaccctcacc ccacccatc ccctccagtg         1000 ggcaactggg ttgggtcagg agggaaaac cccctaggga gacactccat         1050
atactgccca gaccaagtta cctgggacca ggccaaccct ctccttcttt        1100
ggtcaaccca ggggaccctg gcaggggccc aggactcaaa ccagtcaagg        1150
gaggggggtc tagtgcccaa cacccaaata tggctcaaga agggcagcaa        1200
cattcctgct gggtggccca gagggaatgc ccccaggtta tataaaacct        1250
gaccagaggg acaagctgcc accaaaggtg ggatccccat gccactctgg        1300
gtgttcttct ttgtgatcct caccctcagc aacagctccc actgctcccc        1350 acctcccct tgaccctca ggatgaggag atatgcagat gccatcttca         1400
ccaacagcta caggaaggtt ctgggccagc tgtctgccag gaagctgctc        1450
caggacatca tgagcaggca gcagggagag agcaaccaag agagaggagc        1500
aagggcaaga cttggtaggc aagtagacag catgtgggca gaacaaaagc        1550
aaatggaatt ggagagcatc ctggtggccc tgctgcagaa gcacagcagg        1600
```

```
aactcccagg gatgaagatt cctcctgtga ccagggaatt cctgtagcca    1650
aaatgcaact ggatccagtt aatcctctca tttctgaccc acttttcct    1700
ttgaaaatac aataaaattc ccccatacag gtgtgcattt aaagcccatg    1750
gctccaattt tttaataaca ccacccctca tctaccccaa actactgaga    1800
atctaattat atctacattc acttacatat ccatctccac cctccctcaa    1850
tagtctctac accagatgtt gtcttatatt gtttacctt catacacttt    1900
catatcttac aacctttcca tcctatccaa acaaattatc acaccatcta    1950
actaacactg atagaaccaa tacttatcac ttctcactca tacaaaccaa    2000
ttccaacaaa aaaccaccat cacacctacc aatccctaac atacccccct    2050
caatctaata tattctttaa ataaacttta aatatcccaa atactccttc    2100
cttatacccct aaacagtgtt aatagtcatc tgtcccacct ttttttccca    2150
tactagtcac cctccaacac cagctgactc tccctgactg gcttgtctgc    2200
tccaggcatc agcttacaga caagctgtga agtctcctgg agctgcatgt    2250
gtcagaggtt ttcacagtca tcacagaaac tggctagact aaagggccta    2300
gtgatactcc tattttata ggttaatgtc atgataataa tggtttctta    2350
gaagtcaggt ggcacttttc tgggaaatgt gctctgaacc cctatttgtt    2400
tattttcta aatacattca aatatgtatc agctcatgag acaataaccc    2450
tgataaatgc ttcaataatc ctcagtaata caaggggtgt taggtaccaa    2500
tgagccatat tcaagggaaa acttcttgct ctaggccaag attaaattcc    2550
aacatggatg ctgatttata tgggtataaa tgggctagag ataatgttgg    2600
gcaatcaggt gcaacaatct atagattgta tgggaagcca gatgctccag    2650
agttgtttct gaaacatggc aaaggtagtg ttgccaatga tgttacagat    2700
gagatggtca gactaaactg gctgacagaa tttatgcctc ttcctaccat    2750
caagcatttt atcaggactc ctgatgatgc atggttactc accactgcta    2800
tccctgggaa aacagcattc caggtattag aagaatatcc tgattcaggt    2850
gaaaatattg ttgatgctct ggcagtgttc ctgaggagat tgcattctat    2900
tcctgttgt aattgtccctt ttaacagtga tagagtattt agactggctc    2950
aggcacaatc aagaatgaat aatggtttgg ttgatgctag tgattttgat    3000
gatgagagga atggctggcc tgttgaacaa gtctggaaag aaatgcataa    3050
gcttttgcca ttctcacagg attcagttgt cactcatggt gatttctcac    3100
ttgataacct tattttgat gaggggaaat taataggttg tattgatgtt    3150
ggaagagttg gaatagcaga cagataccag gatcttgcca tcctatggaa    3200
ctgccttggt gagtttctc cttcattaca gaagaggctt tttcaaaaat    3250
atggtattga taatcctgat atgaataaat tgcagtttca tttgatgctg    3300
gatgagtttt tctaatcaga attggttaat tggttgtaac actggcaacc    3350
agtgagtgtg ggtcttgcag tatcattgca gcactgggc cagatggtaa    3400
gccctccttg ggatcccaca gagctcaaga tcaaggatc ttcttgagat    3450
ccttttttc tgagagtaat ctgctgcttg caaacaaaaa aaccacagct    3500
accagaggtg gtttgtttgc aggatcaaga gctaccaact cttttcaga    3550
aggtaactgg cttcagcaga gagcagatac caaatactgt ccttctagtg    3600
```

| | | | | | |
|---|---|---|---|---|---|
| tagcagtagt | taggccacca | cttcaagaac | tctgtagcac | agcctacata | 3650 |
| cctagctctg | ctaatcctgt | taccagtggc | tgctgccagt | ggagataagt | 3700 |
| agtgtcttac | agggttggac | tcaagaagat | agttacagga | taaggagcag | 3750 |
| aggtagggct | gaaagggggg | ttagtgcaca | cagcccagct | tggagagaaa | 3800 |
| gacctacaca | gaactgagat | acctacagag | tgagctatga | gaaagagcca | 3850 |
| agcttccaga | agggagaaag | gaggacaggt | atcaggtaag | aggcagggta | 3900 |
| ggaacaggag | agagcaagag | ggagcttcca | gggggaaaag | cctggtatct | 3950 |
| ttatagtcct | gtagggttta | gccacctctg | acttgagagt | agatttttgt | 4000 |
| gatgctagtc | aggggggagg | agcctatgga | aaaaagccag | caaagaggca | 4050 |
| tgc | | | | | 4053 |

METHODS AND COMPOSITIONS FOR GENE THERAPY AND GHRH THERAPY

CROSS-REFERENCE TO RELATED APPLICATIONS

This application is related to a U.S. patent application filed on an even date herewith: "Treatment of Infection Using Single Chain Antibody Gene Therapy", filed as a U.S. Non-provisional patent application Ser. No. 13/298,251.

REFERENCE TO SEQUENCE LISTING, COMPUTER PROGRAM, OR COMPACT DISK

The instant application contains a Sequence Listing which has been submitted in ASCII format via EFS-Web and is hereby incorporated by reference in its entirety. Said ASCII copy, created on Sep. 16, 2011, is named "Sequence listing.txt" and is 53,705 bytes in size.

FIELD OF THE INVENTION

The present invention relates to DNA constructs for in-vivo production of growth hormone releasing hormone (GHRH), and to methods for minimizing activation of the immune system by any DNA constructs introduced into mammalian tissues where the constructs are brought by normal biological mechanisms into the nucleus of cells. A preferred method of introduction of DNA constructs uses plasmids.

GENERAL BACKGROUND AND OBJECTS OF THE INVENTION

A number of publications exist for various forms of GHRH-coding DNA plasmid constructs including patents for a product currently marketed for veterinary use in Australia under the name Lifetide® by VGX PHARMACEUTICALS, LLC out of Blue Bell, Pa., a company acquired by Inovio Pharmaceuticals of Blue Bell, Pa.

There are two major conventional methods of gene therapy, the first, generally better known method, is to use viral capsids to encapsulate a DNA sequence of interest for introduction into animal tissue. Such viral capsids are generally termed viral vectors, and a variety of vectors have been used including HIV and adenoviruses. Such viral vectors are generally constructed so that they should not reproduce in-vivo, and usually contain a reverse transcriptase that results in splicing of the viral vector borne DNA into the host animal's genome.

The viral vector method has multiple drawbacks, not least of which is that it has caused patient death and serious illness, both short term (e.g. idiopathic apparent immune system storm) and long term (e.g. cancer), despite the relative rarity of this type of gene therapy's use. One patient has also died due to the gene of interest resulting in sufficient immune system suppression that a probably quiescent infection to bloom. Thus, while gene therapy had been perceived as having much promise, there are issues, most of which have little to do with the genes of interest that are introduced.

By contrast, the second major conventional method of gene therapy, DNA gene therapy, uses the much simpler method of injection of DNA into the patient. This introduces considerably less packaging material into the host, and DNA constructs are generally smaller. DNA is not incorporated into the host genome, but is instead maintained separately in circlets either inside the nucleus or at the nuclear wall inside the cell. These circlets may become associated with histones within the nucleus. However, DNA gene therapy has few inherent problems. DNA gene therapy does suffer from difficulty producing enough of the gene product. It also may have a small percentage of subjects who are stimulated to produce an immune response to the protein product of the gene of interest. This effect is due to the self-adjuvant effect of plasmids, which contain gene sequence motifs which are recognized by animal immune systems as having a non-self origin. These motifs contain cytosine followed by guanine in the 5' to 3' direction, also called CpG sequences (Brazalot-Millan et al, 1998).

Because GHRH has a half-life after injection of roughly 8 minutes, it has not been practical to supplement using conventional methods. However, GHRH is a peptide hormone, which makes DNA gene therapy a viable alternative for supplementation. In addition, GHRH is a hormone that is required in very small amounts. These three factors together make it an appropriate choice to consider for DNA gene therapy.

Thus, there is a need to improve GHRH gene constructs. The present invention minimizes immune system activation by anti-adjuvant codon optimization to eliminate CpG sequences to prevent binding to bacterial DNA intracellular receptors.

In addition, methods and compositions are provided that further minimize the activation of the immune system by any DNA construct delivered in-vivo using co-delivered compounds (Yu et al, 2008).

The Applicant further provides compositions for improved regulation and expression of the plasmids by means of AT rich regions that are in the range of 20 base pairs to 1000 base pairs long placed 5' and 3' to the gene expression cassette.

There are further compositions to improve secretion of the produced protein by providing a leader sequence on the gene which codes for a peptide that signals the cell to transport the gene product to the cell membrane for export. (Zou, 2006)

And finally, there is postproduction modification of plasmids to excise the bacterial components so as to yield a smaller circlet of DNA bearing the expression cassette only. This allows use of higher yield bacterial origins of replication containing large CpG sequences so as to get higher concentration of plasmid in production, while preventing the shutdown of plasmid gene expression that is associated with DNA bearing bacterial sequences.

It is therefore a primary object of the invention to improve suitability of GHRH constructs for human therapeutic use.

It is a further object of the invention to provide methods for minimizing immunogenicity of DNA constructs delivered into cells.

It is a further object of the invention to provide methods for maximizing ongoing expression of DNA constructs delivered into cells.

Other objects and advantages of the present invention will become apparent to the reader and it is intended that these objects and advantages are within the scope of the present invention.

As a practical matter, when expanding cultures of bacteria to reproduce usable quantities of plasmids for gene therapy, minor mutations occur, most of which are of no significance. In this invention, such mutations are only significant when they result in changes that create antigenic responses not created by the designed plasmid or else functional modification of the peptide sequence for the GHRH gene.

SUMMARY OF THE INVENTION

This present invention provides a set of constructs for delivering DNA coding for GHRH into cells. These constructs are completely or mostly free of what are termed CpG sequences as well as larger bacterial DNA motifs that have been identified as having adjuvant activity to minimize immune activation. A CpG sequence is a 5' to 3' cytosine linked by a deoxyribose sugar phosphate to a guanine in a nucleotide sequence.

The present invention also uses an anti-inflammatory as an anti-adjuvant that may be either delivered together with the DNA or else separately as an oral or injected treatment. The primary anti-adjuvant compound, hereinafter referred to as DOI, is 2,5-dimethoxy-4-iodoamphetamine, also (1-(2,5-dimethoxy-4-iodophenyl)-2-aminopropane) and congeners. DOI is currently the strongest anti-inflammatory with published data, a therapeutic dosage level being generally in a range from approximately 1 to 3 micrograms per kilogram. Other anti-inflammatory compounds may also be used. An advantage of DOI is that it is long acting, with a rough half-life of 12-15 hours, giving it a therapeutic effect for 30 hours or more. For co-injection, powerful, long acting agents that counter cytokines and chemokines which signal the immune system are optimum for use as anti-adjuvants because the stronger they are the less material needs to be injected.

The provision of DOI or some other anti-adjuvant agent may be enhanced by delivery of the material impregnated into microbeads that are present in the mixture when it is injected. These microbeads are preferably in a range of size within several microns of 2 micrometers in diameter since this roughly 2 micron size is optimal for uptake by animal cell membranes. Microbeads of other suitable sizes may be used as well. Microbeads may be made from various materials, including polyethylene glycol (PEG) and poly-lactide-co-glycolide (PLG) (Vila et al, 2002; Tracy et al, 1999). This provides a time release of the agent intracellularly where it is most needed and extends the amount of time the agent is active. Such microbeads, themselves, have a degree of adjuvant effect, so the inclusion of DOI or other anti-adjuvant counteracts the adjuvant effect of the beads while allowing certain advantages of bead-based delivery to be retained. Thus, provision of an anti-adjuvant in microbeads is a significant improvement on the art.

In addition, microbeads may optionally have a non-antigenic fluorophore or a radioactive material such as gallium radioisotope impregnated into them in order to track the location in the body where the beads are taken up. Finally, DNA plasmids may optionally be adsorbed onto the surface of beads or impregnated into the beads to enhance uptake by animal cells.

Most of the constructs contain a promoter specific to the intended target, which are muscle cells. Muscle cells are targeted because they have relatively high metabolism and higher rates of protein synthesis. The promoters used in these constructs are myosin promoters, however, any promoter that expresses with specificity in muscle cells could be used. The purpose of this feature of the constructs is to minimize or eliminate expression of the gene product in cells which are not the intended target. Non-specific promoters such as variants on the cytomegalovirus (CMV) promoter produce proteins of interest when they are taken up by antigen-presenting cells (APCs). Such APCs can then present to the immune system the peptides originating from the gene of interest in the construct, which can lead to the unwanted result of an immune system response against the gene product. The invention disclosed herein has as one of its foundations immune system optimization, which means in this context, that the sequence is optimized so that it minimizes stimulation of the immune system.

The constructs of this invention comprise one or more AT rich regions that are 5' or 3' to the expression cassette. These AT rich regions help to improve the expression in animal cells of the gene carried by the plasmid. These AT rich regions avoid start codons in order to prevent the presence of an open reading frame (ORF). Certain sequences of AT rich regions were also developed on the basis of literature showing efficacy, but redesigned to conform with the immune system optimization of the present invention.

In some cases it may be desirable to remove the sections of the plasmid which are required for reproduction of the plasmid in bacterial cells. This generally requires cutting the plasmid with a set of endonucleases and ligating the resulting circlets. This removal could also be accomplished by use of topoisomerase methods.

The advantages of the Applicant's system are that the system (1) removes all or most immune system triggers from the DNA construct itself, (2) suppresses immune system responses locally and systemically, (3) minimizes or eliminates presentation of the gene of interest to the immune system, (4) stabilizes long-term expression of the plasmid in-vivo, (5) for maximizing production of plasmid in bacteria and removal of the antigenic bacterial sequences prior to injection, and (6) provides the gene product, GHRH.

A first and preferred embodiment of the Applicant's invention is a DNA plasmid construct containing a bacterial plasmid without CpG sequences (for the purpose of immune system optimization) comprising a promoter, an antibiotic resistance gene, a tissue specific promoter, a secretion signal peptide, a peptide sequence GHRH gene, a poly-A gene terminator, and one or more flanking AT rich regions between the bacterial section and the mammalian expression section of the plasmid, as shown in FIG. 2. This construct is delivered into muscle cells together with DOI at a dose generally above 0.5 micrograms per kilogram, dissolved into water and salts medium.

Other embodiments of the Applicant's invention are possible and are discussed below. One embodiment which is of special interest is the alternate embodiment shown in FIGS. 1a and 1b. These figures show how the invention could be grown within any generic plasmid in any suitable bacteria (e.g. yeast) and post processed after purification to separate the therapeutic segment of the invention.

A similar strategy to that shown in FIGS. 1a and 1b removes only the bacterial origin of replication from the plasmid, instead of all elements pertaining to the bacteria. This is useful because the shorter segment can be more amenable to removal by topoisomerase, and generally it is the bacterial origin of replication that has the greatest impact on copy number.

This invention provides, for the first time, a system that minimizes host immune response while providing persistent high activity for delivered GHRH gene therapy and hence makes gene therapy for GHRH in humans a practical matter. It also provides, for the first time, a practical system for minimizing host immunity with any DNA construct delivered into cells by making use of an anti-adjuvant compound.

In vaccines, the study of adjuvants, which are materials that enhance immune system response, is a field which has yielded benefits. This application breaks ground with the invention of anti-adjuvants as a class of compounds. An anti-adjuvant is a material or method that interferes with host immunity occurring in response to an injection.

BRIEF DESCRIPTION OF THE FIGURES

The foregoing aspects and many of the attendant advantages of the invention will become more readily appreciated as the same becomes better understood by reference to the following detailed description, when taken in conjunction with the accompanying drawings, wherein.

DETAILED DESCRIPTION OF THE INVENTION

The Applicant discloses several embodiments and provides guidance for aspects of the method to be applied to other situations.

Figures 1A, 1B:
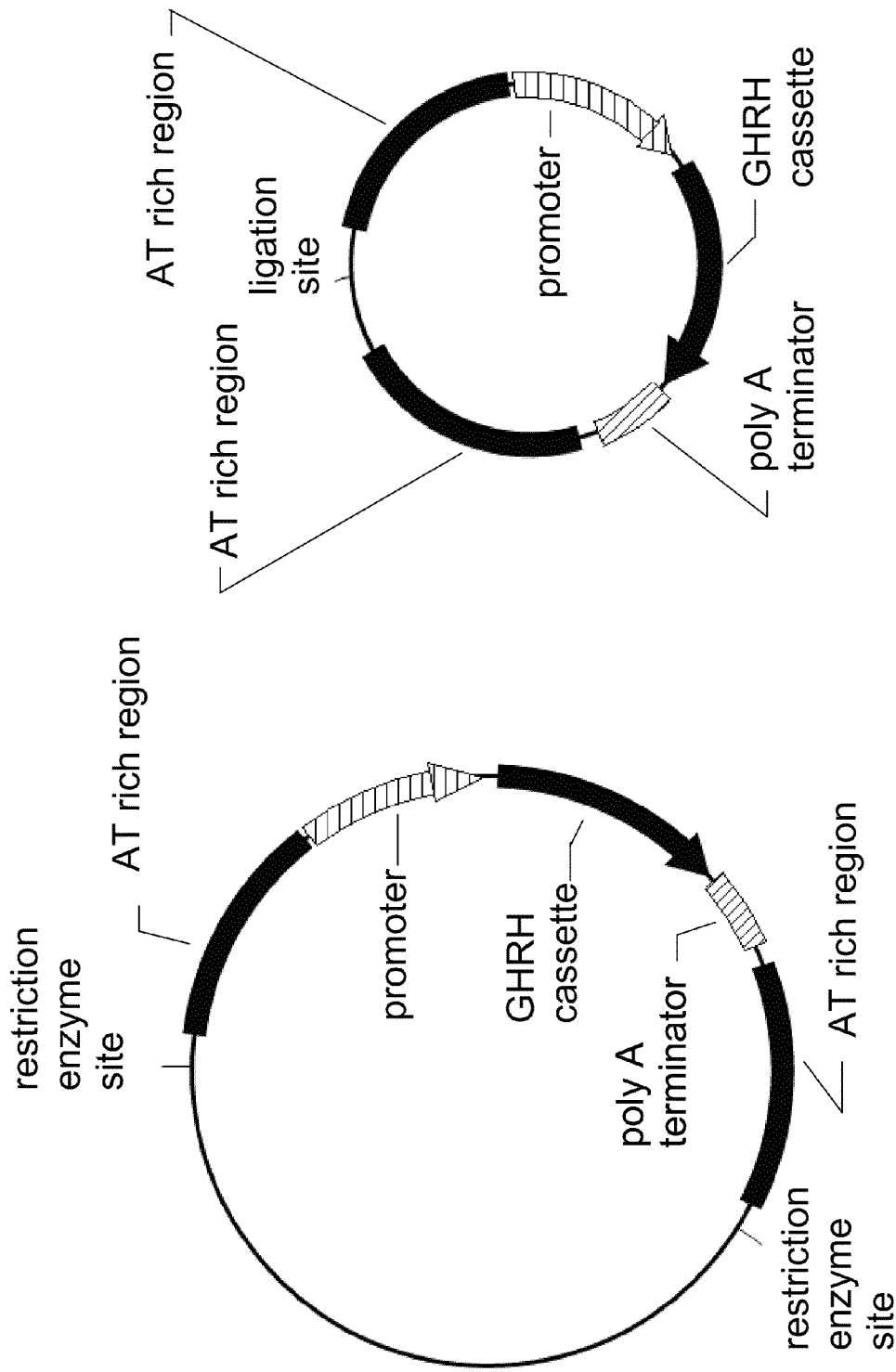
FIG. 1a is a diagram of generic plasmid containing the most basic features of the invention.
FIG. 1b is a diagram of a post-processed minimum therapeutic circlet.

FIG. 1a is a diagram of generic plasmid containing the most basic features of the invention. There is a promoter and a poly-A terminator flanking the gene cassette, and these are, in turn, flanked by AT rich regions. Specific restriction enzyme sites are present to allow separation of the active therapeutic parts of the plasmid invention from the inactive parts. In practice, all of the regions shown may be spliced into virtually any generic plasmid, which may be raised in any suitable bacteria.

FIG. 1b is a diagram of a post-processed minimum therapeutic circlet. In FIG. 1a the plasmid comprises two restriction enzyme sites flanking the AT rich regions. Use of restriction enzymes followed by re-ligation of the sticky ends results in a circlet of DNA composed only of the active components. Said re-ligation of the sticky ends may occur by means of a linker with compatible, but different, sticky ends. The whole process may occur in one step by use of a topoisomerase system, and in that case the restriction enzyme sites of FIG. 1a would be replaced by suitable sequences necessary for the topoisomerase to function. Thus, using this method of post-processing into a circlet, the large section of the plasmid which is only present so that it can reproduce within suitable bacteria may be dispensed with. This allows the zero CpG strategy to be pursued using any standard plasmid, whether or not the plasmid has been optimized. It has been shown that such small circlets of DNA perform better in mammalian cells.

Figure 2:
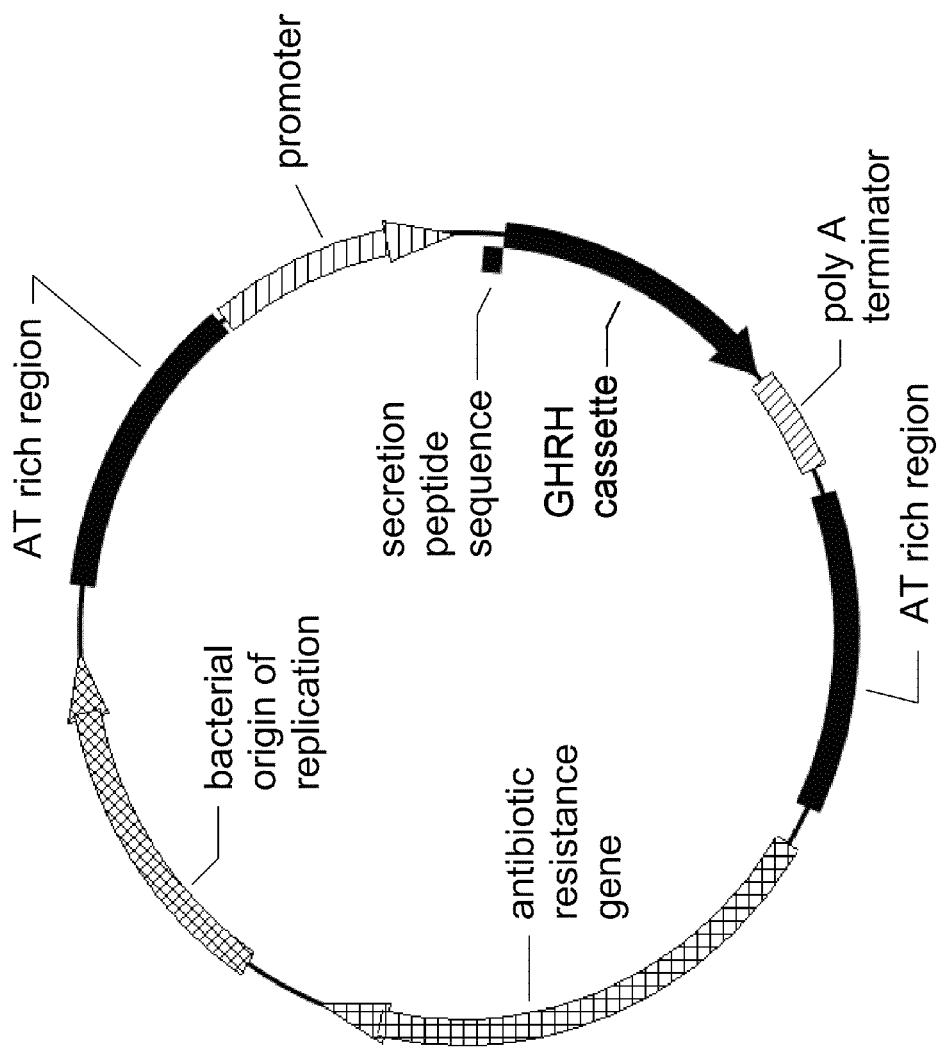
FIG. 2 is a diagram of the invention wherein additional optional components are shown.

FIG. 2 is a diagram of the invention wherein additional optional components are shown. There are multiple implementations of the antibiotic resistance gene claimed, and any of these could take the place of the generic antibiotic resistance gene shown. There are multiple implementations of the bacterial origin of replication claimed, and any of these could take the place of the generic bacterial origin of replication claimed. A secretion sequence is claimed for the invention and this is optionally present. Such a secretion sequence is shown at the 5' end of the GHRH cassette; however, its location may vary as appropriate for the secretion sequence chosen. In this diagram the AT rich regions may have sequences that vary as claimed. A significant feature of the AT rich regions is that they not generally contain CpG sequences.

A first and preferred embodiment of the present invention is a DNA plasmid construct containing a bacterial plasmid origin of replication that does not contain CpG sequences, a bacterial antibiotic resistance gene that does not contain CpG sequences, a myosin promoter containing no CpG sequences, a human peptide sequence GHRH gene that contains no CpG sequences, a poly-A termination sequence containing no CpG sequences, and one or more AT rich regions between the bacterial section and the mammalian expression half of the plasmid which also contain no CpG sequences. This construct is delivered into muscle cells together with DOI at a dose generally above 0.5 micrograms per kilogram, dissolved into a water and salts medium suitable for preservation of DNA.

In an alternative embodiment, the invention is identical to the first embodiment with the exception that the bacterial promoter is of a standard variety that does contain CpG sequences. This alternative embodiment may have the bacterial promoter flanked by restriction enzyme or topoisomerase sites for the purpose of removing the CpG sequences from the final therapeutic product. It may be desired to make use of an affinity surface to which is bonded nucleotide sequences compatible with the sticky ends of the section of the plasmid which is removed. This method can be used to purify the final product.

In a second alternative embodiment, the invention is nearly identical to one of the first two embodiments with the difference that the host cell promoter is CMV or some other high activity general promoter. Generally, this promoter would be immune system optimized by removal of CpG sequences.

In a third alternative embodiment, the cassette is one of several contained within a super-cassette designed to deliver more than one gene therapy. An example of how this could be accomplished is by use of the CHYSEL system (P. de Felipe, 2004).

In a fourth alternative embodiment, the invention utilizes microbeads impregnated with DOI in a solution generally containing small quantities of DOI as the vehicle for delivering any vector. This embodiment could also, potentially, adsorb the DNA vector onto the surface of the beads or impregnate the beads with the vector. These microbeads may generally be made from poly (lactide co-glycolide) (PLG), polyethylene glycol (PEG) or a combination. The microbeads may contain other materials, for instance to regulate pH.

In typical operation, a solution containing double distilled or molecular biology grade water with a suitable DNA preservation buffer, which may contain a suitable protease to preserve a single dose of the DNA construct, may be mixed in a small bottle or tube with between 80 and 250 micrograms of DOI. This mixture may then be vacuum dried (lyophilized) to stabilize it for storage. After drying, the bottles or tubes may be sealed and stored at a temperature of 4° C. or lower. The invention may be shipped in an insulated cool container with ice to keep it from overheating. (However, the invention should be quite stable at room temperature or above, thus making it suitable for use in the developing world where refrigeration is often lacking) To use the invention, it may be mixed with an appropriate quantity of distilled or molecular biology grade water, then drawn into a syringe and injected directly into a muscle which is well used and has a high metabolic rate, such as the gastrocnemius. In some patients a different muscle might be chosen to maximize activity. Prior to injection, the muscle may be chilled with ice packs to as low a temperature as practical without freezing or causing other cold damage to the patient. After injection, the ice pack may be reapplied for a period of up to approximately 1 hour. To improve DNA transfer into cells, the injector used may have a set of 3 or more very sharp needles surrounding it extending to the same depth as the primary injector needle and a series of microsecond pulses of direct current to electroporate the DNA into the muscle cells more efficiently may be applied after completely pressing down the plunger.

In alternative operations of the invention, there may not be electroporation, or the muscle may not be cooled. Different preservation methods may be used for the DNA as well, and variants on the injector may include a gene gun applied directly to the muscle after exposing the muscle through a small incision. In addition, for some patients, injecting a numbing agent may be desirable, however, generally this would not be done into the area of the gene injection, but would be a nerve block with a 1-2 hour action.

Additional alternatives of the invention may be described as follows:

a. a cell and optionally a myoblast may be transformed in vitro with a vector for expression of a nucleic acid sequence in a cell, the vector comprising a nucleic acid cassette comprising a nucleotide sequence encoding a human sequence growth hormone releasing hormone ("GHRH"); a first 5' flanking region to said nucleic acid cassette including one or more promoter sequences for expression of said nucleic acid cassette; a second 5' region flanking said promoter sequences at any distance from said promoter, wherein said second 5' flanking region contains between 20 and 2000 nucleotides comprising AT rich sequences wherein said second 5' flanking region contains no CpG sequences; a first 3' flanking region to the nucleic acid cassette at any distance from said cassette, wherein said first 3' flanking region contains between 20 and 2000 nucleotides with AT rich sequences wherein said first 3' flanking region contains no CpG sequences; and wherein said human GHRH cassette has the sequence of SEQ ID NO: 1, 2, 3, 4 or 5.

b. A method of administration of the GHRH treatment wherein a plurality of said cells from paragraph (a) are delivered into the muscle of a living animal.

c. A method for transfection of a muscle cell in vivo, comprising the step of administering directly to said cell the vector of paragraph (a) leading to transfection of said cell.

d. A method for delivery and expression of a GHRH gene in a plurality of muscle cells, comprising the steps of: (a) administering directly to said plurality of muscle cells the vector of paragraph (a); and (b) incubating said plurality of muscle cells under conditions that allow the expression of the nucleotide sequence encoding the GHRH in said vector. In additional embodiments the cells of this paragraph are human cells, and in additional embodiments said cells are chilled in vivo below normal body temperature for a minimum of 5 minutes prior to administering said vector, and said cells are maintained below normal body temperature for a minimum of 10 minutes after administration of said vector.

e. The vector of paragraph (a), wherein said vector comprises a nucleotide sequence which is the same as the nucleotide sequence of plasmid p80715-5.1 which has the sequence of SEQ ID NO: 23.

f. The vector of paragraph (a), wherein said vector comprises a nucleotide sequence which is the same as the nucleotide sequence of plasmid p80716-B6.1 which has the sequence of SEQ ID NO: 24.

g. The vector of paragraph (a), wherein said vector comprises a nucleotide sequence which is the same as the nucleotide sequence of plasmid p80717-B7.1 which has the sequence of SEQ ID NO: 25.

h. The vector of paragraph (a), wherein said vector comprises a nucleotide sequence which is the same as the nucleotide sequence of plasmid p80718-B8.1 which has the sequence of SEQ ID NO: 26.

i. The vector of paragraph (a), wherein said vector comprises a nucleotide sequence which is the same as the nucleotide sequence of plasmid p80715-5.2 which has the sequence of SEQ ID NO: 27.

j. The vector of paragraph (a), wherein said vector comprises a nucleotide sequence which is the same as the nucleotide sequence of plasmid p80716-B6.2 which has the sequence of SEQ ID NO: 28.

k. The vector of paragraph (a), wherein said vector comprises a nucleotide sequence which is the same as the nucleotide sequence of plasmid p80717-B7.2 which has the sequence of SEQ ID NO: 29.

l. The vector of paragraph (a), wherein said vector comprises a nucleotide sequence which is the same as the nucleotide sequence of plasmid p80718-B8.2 which has the sequence of SEQ ID NO: 30.

In yet other alternative embodiments, the following sequences are disclosed:

a. The sequence of SEQ ID NO: 3, an immune system optimized human GHRH gene.

b. The sequence of SEQ ID NO: 4, an immune system optimized human GHRH gene.

c. The sequence of SEQ ID NO: 5, an immune system optimized human GHRH gene.

d. The sequence of SEQ ID NO: 7, an immune system optimized human actin alpha 1 promoter.

e. The sequence of SEQ ID NO: 9, an immune system optimized expression enhancer.

f. The sequence of SEQ ID NO: 10, an immune system optimized expression enhancer.

g. The sequence of SEQ ID NO: 11, an immune system optimized an expression enhancer.

h. The sequence of SEQ ID NO: 12, an immune system optimized an expression enhancer.

i. The sequence of SEQ ID NO: 13, an immune system optimized antibiotic resistance gene.

j. The sequence of SEQ ID NO: 14, an immune system optimized antibiotic resistance gene.

k. The sequence of SEQ ID NO: 15, an immune system optimized antibiotic resistance gene.

l. The sequence of SEQ ID NO: 16, an immune system optimized antibiotic resistance gene.

m. The sequence of SEQ ID NO: 17, an immune system optimized antibiotic resistance gene.

n. The sequence of SEQ ID NO: 18, an immune system optimized antibiotic resistance gene.

o. The sequence of SEQ ID NO: 19, an immune system optimized R6K origin of replication.

p. The sequence of SEQ ID NO: 21, an immune system optimized R6K origin of replication.

q. The sequence of SEQ ID NO: 22, an immune system optimized pBR322 origin of replication.

The invention as it relates to anti-adjuvants as exemplified by DOI has wide application for plasmid gene therapy. The step of chilling muscles pre-injection and post-injection as an anti-adjuvant method also has wide application for plasmid gene therapy.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

I claim:

1. A vector for delivering a nucleic acid sequence into a living organism, wherein said vector has the sequence of SEQ ID NO: 23, 24, 25, 26, 27, 28, 29, or 30.

2. The vector of claim 1 wherein said vector is delivered together with an anti-adjuvant compound that minimizes or prevents immune system response.

3. A vector for expression of a nucleic acid sequence in a cell, the vector comprising:
   c. a nucleic acid cassette comprising a nucleotide sequence encoding a human growth hormone releasing hormone ("GHRH");
   d. a first 5' flanking region to said nucleic acid cassette including one or more promoter sequences for expression of said nucleic acid cassette;
   e. a second 5' region flanking said promoter sequences at any distance from said promoter, wherein said second 5' flanking region contains between 20 and 2000 nucleotides comprising AT rich sequences wherein said second 5' flanking region contains no CpG sequences;
   f. a first 3' flanking region to the nucleic acid cassette at any distance from said cassette, wherein said first 3' flanking region contains between 20 and 2000 nucleotides with AT rich sequences wherein said first 3' flanking region contains no CpG sequences; and
   g. wherein said human GHRH cassette has the sequence of SEQ ID NO: 1, 2, 3, 4 or 5.

4. The vector of claim 3 wherein said vector is delivered together with an anti-adjuvant compound that minimizes or prevents immune system response.

5. The vector of claim 3 wherein said vector is delivered together with an anti-adjuvant compound.

6. The vector of claim 1 wherein said vector is delivered together with an anti-adjuvant compound which is DOI.

* * * * *